US008530182B2

(12) United States Patent
Barr et al.

(10) Patent No.: US 8,530,182 B2
(45) Date of Patent: Sep. 10, 2013

(54) VIRAL PROTEIN QUANTIFICATION PROCESS AND VACCINE QUALITY CONTROL THEREWITH

(75) Inventors: John R. Barr, Suwanee, GA (US); Tracie L. Williams, Atlanta, GA (US); Leah G. Luna, Sanford, MI (US); Zhu Guo, Atlanta, GA (US); Rubin Donis, Atlanta, GA (US); James L. Pirkle, Atlanta, GA (US)

(73) Assignee: Centers for Disease Control and Prevention, Atlanta, GA (US)

( * ) Notice: Subject to any disclaimer, the term of this patent is extended or adjusted under 35 U.S.C. 154(b) by 101 days.

(21) Appl. No.: 12/746,649

(22) PCT Filed: Dec. 5, 2008

(86) PCT No.: PCT/US2008/013396
§ 371 (c)(1),
(2), (4) Date: Apr. 15, 2011

(87) PCT Pub. No.: WO2009/110873
PCT Pub. Date: Sep. 11, 2009

(65) Prior Publication Data
US 2011/0201039 A1    Aug. 18, 2011

Related U.S. Application Data

(60) Provisional application No. 60/992,520, filed on Dec. 5, 2007.

(51) Int. Cl.
*C12Q 1/37* (2006.01)

(52) U.S. Cl.
USPC .......................................................... 435/23

(58) Field of Classification Search
None
See application file for complete search history.

(56) References Cited

U.S. PATENT DOCUMENTS

| | | | |
|---|---|---|---|
| 6,322,970 B1 | 11/2001 | Little et al. | |
| 6,927,031 B2 | 8/2005 | Lu et al. | |
| 2003/0153523 A1 | 8/2003 | Rana | |
| 2005/0118666 A1 | 6/2005 | Sakai et al. | |
| 2006/0051742 A1* | 3/2006 | Kapteyn et al. | 435/5 |
| 2007/0072192 A1 | 3/2007 | Edwards et al. | |

FOREIGN PATENT DOCUMENTS

| | | |
|---|---|---|
| EP | 1010008 A2 | 6/2000 |
| EP | 1666884 A1 | 6/2006 |
| GB | 2404194 A | 1/2005 |
| JP | 2006300758 A | 11/2006 |
| WO | 96/41172 A1 | 12/1996 |
| WO | 9734613 A1 | 9/1997 |
| WO | 9912040 A2 | 3/1999 |
| WO | 2007/109370 A2 | 9/2007 |
| WO | 2009110873 A2 | 9/2009 |

OTHER PUBLICATIONS

Barnidge et al., "Absolute Quantification of the G Protein-Coupled Receptor Rhodopsin by LC/MS/MS Using Proteolysis Product Peptides and Synthetic Peptide Standards", Analytical Chemistry, vol. 75, No. 3, Feb. 1, 2003, pp. 445-451.*
Anderson et al., "Quantitative Mass Spectrometric Multiple Reaction Monitoring Assays for Major Plasma Proteins", Molecular & Cellular Proteomics, 2005, vol. 5, No. 4, pp. 573-588.*
Ong et al., "Mass spectrometry—based proteomics turns quantitative", Nature Chemical Biology, 2005, 1(5):252-262.*
Bandeira et al.; Protein Identification by Spectral Networks Analysis; The National Academy of Sciences of the USA; Apr. 2007; pp. 6140-6145.
Barr et al; Isotope Dilution-Mass Spectrometric Quantification of Specific Proteins: Model Application with Apolipoprotein A-I; Clinical Chemistry 42:10; (1996); pp. 1676-1682.
Kirkpatrick et al; The Absolute Quantification Strategy: a General Procedure for the Quantification of Proteins and Post-Translational Modifications; Science Direct; (2005) pp. 265-273.
Wiltshire et al.; Development of a High-Performance Liquid Chromatographic-Mass Spectrometric Assay for the Specific and Sensitive Quantification of Ro 64-0802, an Anti-Influenza Drug, and its Pro-Drug, Oseltamivir, in Human and Animal Plasma and Urine; Journal of Chromatography B; (2000) pp. 373-388.
Viveka Mayya et al.; Absolute Quantification of Multisite Phosphorylation by Selective Reaction Monitoring Mass Spectrometry; The American Society for Biochemistry and Molecular Biology, Inc.; (2006), pp. 1146-1157.
Bethny Morrissey et al.; Antigenic Characterisation of H3N2 Subtypes of the Influenza Virus by Mass Spectrometry; ScienceDirect (2007); pp. 106-114.
Stuart J. Rodda et al; The Single Radial Immunodiffusion Assay Highlights Small Antigenic Differences Among Influenza Virus Hemagglutinins; Journal of Clinical Microbiology, Nov. 1981; pp. 479-482.
Alejandro Wolf-Yadlin et al; Multiple Reaction Monitoring for Robust Quantitative Proteomic Analysis of Cellular Signaling Networks; PNAS (2007); vol. 104, No. 14; pp. 5860-5865.
Barnidge David. R et al.; Absolute quantification of the G protein-coupled receptor Rhodopsin by LC/MS/MS using proteolysis product peptides and synthetic peptide standards; Analytical Chemistry; American Chemical Society, U.S., vol. 75, No. 3; Feb. 1, 2003; pp. 445-451; XP003012639; ISSN: 0003-2700; DOI: 10.1021/AC026154+.
Bantscheff, Marcus et al.; Quantitative mass spectrometry in proteomics: a critical review; Analytical and Bioanalytical Chemistry, Springer, Berlin, DE; vol. 389, No. 4; Aug. 1, 2007; pp. 1017-1031; XP019537646; ISSN: 1618-2650; DOI: 10.1007/S00216-007-1486-6.
Supplemental European Search Report dated Feb. 27, 2013, for co-pending application No. EP088873186.4.

* cited by examiner

*Primary Examiner* — Suzanne M Noakes
(74) *Attorney, Agent, or Firm* — Gifford, Krass, Sprinkle, Anderson & Citkowski, P.C.; Weston R. Gould

(57) ABSTRACT

A process of quantifying proteins in a complex mixture is provided. The invention has utility in quantifying proteins in a complex preparation of uni- or multivalent commercial or research vaccine preparations.

19 Claims, 9 Drawing Sheets

Amount of H3 in commercial vaccine (fmol/μL)

| Digest 1 | Digest 2 | Digest 3 | Digest 4 | Digest 5 |
|---|---|---|---|---|
| 22.44 | 24.39 | 23.08 | 22.03 | 25.83 |
| 21.93 | 24.40 | 24.60 | 23.49 | 25.18 |
| 20.39 | 22.90 | 24.45 | 23.06 | 25.45 |
| 24.12 | 23.91 | 24.41 | 24.06 | 24.99 |
| Digest 6 | Digest 7 | Digest 8 | Digest 9 | Digest 10 |
| 19.08 | 19.49 | 21.32 | 20.76 | 22.02 |
| 21.65 | 21.89 | 22.51 | 21.27 | 22.58 |
| 23.36 | 22.47 | 20.69 | 21.90 | 18.33 |
| 22.35 | 19.30 | 21.89 | 22.68 | 21.98 |
| Digest 11 | Digest 12 | Digest 13 | Digest 14 | Digest 15 |
| 21.77 | 20.45 | 18.81 | 19.61 | 21.97 |
| 23.07 | 21.46 | 20.83 | 21.06 | 21.55 |
| 22.05 | 23.39 | 21.50 | 20.57 | 20.66 |
| 22.06 | 22.00 | 21.86 | 21.72 | 19.93 |
| Digest 16 | Digest 17 | Digest 18 | Digest 19 | Digest 20 |
| 22.98 | 23.16 | 19.43 | 22.25 | 22.74 |
| 20.77 | 20.39 | 22.68 | 23.24 | 20.72 |
| 21.08 | 22.11 | 20.64 | 21.40 | 20.65 |
| 20.76 | 22.20 | 21.25 | 22.54 | 22.82 |

Mean 22.03
Std. dev. 1.24
%RSD 5.61

Amount of H1 in commercial vaccine (fmol/uL)

| Digest 1 | Digest 2 | Digest 3 | Digest 4 | Digest 5 |
|---|---|---|---|---|
| 32.31 | 32.23 | 34.10 | 33.65 | 33.40 |
| 32.37 | 32.27 | 34.08 | 33.00 | 33.46 |
| 35.37 | 32.76 | 33.31 | 33.69 | 33.51 |
| 34.11 | 32.93 | 34.30 | 31.46 | 32.36 |
| Digest 6 | Digest 7 | Digest 8 | Digest 9 | Digest 10 |
| 33.89 | 33.95 | 31.81 | 35.13 | 34.74 |
| 34.87 | 32.51 | 31.37 | 31.89 | 33.05 |
| 33.23 | 32.55 | 30.88 | 32.00 | 35.05 |
| 36.94 | 32.79 | 32.24 | 35.40 | 33.22 |
| Digest 11 | Digest 12 | Digest 13 | Digest 14 | Digest 15 |
| 31.23 | 29.73 | 32.78 | 33.47 | 32.98 |
| 32.28 | 30.99 | 32.46 | 31.39 | 30.99 |
| 32.52 | 30.61 | 30.20 | 32.83 | 31.74 |
| 31.26 | 28.72 | 30.77 | 33.31 | 33.69 |
| Digest 16 | Digest 17 | Digest 18 | Digest 19 | Digest 20 |
| 31.17 | 29.56 | 32.27 | 30.29 | 32.10 |
| 33.02 | 33.31 | 32.31 | 33.08 | 29.42 |
| 32.02 | 30.99 | 30.97 | 30.68 | 32.60 |
| 31.16 | 30.79 | 32.20 | 33.82 | 32.10 |

Mean 32.50
Std. dev. 1.14
%RSD 3.51

Amount of HB in commercial vaccine (fmol/uL)

| Digest 1 | Digest 2 | Digest 3 | Digest 4 | Digest 5 |
|---|---|---|---|---|
| 49.936 | 50.295 | 52.031 | 48.802 | 46.819 |
| 48.476 | 50.720 | 51.702 | 49.297 | 45.969 |
| 49.673 | 51.221 | 47.258 | 48.293 | 44.874 |
| 48.286 | 55.376 | 46.350 | 44.629 | 46.887 |
| Digest 6 | Digest 7 | Digest 8 | Digest 9 | Digest 10 |
| 60.054 | 54.940 | 55.040 | 52.557 | 58.966 |
| 59.659 | 52.192 | 54.962 | 51.183 | 57.193 |
| 58.273 | 54.223 | 48.551 | 53.217 | 56.184 |
| 58.305 | 52.384 | 53.923 | 48.116 | 53.400 |
| Digest 11 | Digest 12 | Digest 13 | Digest 14 | Digest 15 |
| 60.066 | 55.347 | 50.185 | 49.009 | 47.637 |
| 60.002 | 52.137 | 49.292 | 48.022 | 45.975 |
| 58.735 | 52.090 | 49.237 | 47.869 | 45.471 |
| 63.962 | 48.743 | 44.716 | 50.886 | 48.352 |
| Digest 16 | Digest 17 | Digest 18 | Digest 19 | Digest 20 |
| 42.859 | 46.327 | 54.495 | 56.554 | 63.627 |
| 43.558 | 49.114 | 54.078 | 60.284 | 59.358 |
| 42.576 | 48.434 | 48.931 | 54.806 | 58.682 |
| 42.000 | 46.941 | 49.807 | 57.948 | 63.124 |

Mean 51.77
Std. dev. 5.04
%RSD 9.74

SEQUENCE LISTING

```
<160> NUMBER OF SEQ ID NOS: 66

<210> SEQ ID NO 1
<211> LENGTH: 11
<212> TYPE: PRT
<213> ORGANISM: Influenza virus
<220> FEATURE:
<221> NAME/KEY: MISC_FEATURE
<223> OTHER INFORMATION: fragment of conservative region of H1 subtype

<400> SEQUENCE: 1

Glu Gln Leu Ser Ser Val Ser Ser Phe Glu Arg
1               5                   10

<210> SEQ ID NO 2
<211> LENGTH: 12
<212> TYPE: PRT
<213> ORGANISM: Influenza virus
<220> FEATURE:
<221> NAME/KEY: MISC_FEATURE
<223> OTHER INFORMATION: fragment of conservative region of H3 subtype

<400> SEQUENCE: 2

Ser Thr Gln Ala Ala Ile Asn Gln Ile Asn Gly Lys
1               5                   10

<210> SEQ ID NO 3
<211> LENGTH: 7
<212> TYPE: PRT
<213> ORGANISM: Influenza virus
<220> FEATURE:
<221> NAME/KEY: MISC_FEATURE
<223> OTHER INFORMATION: fragment of conservative region of H5 subtype

<400> SEQUENCE: 3

Glu Glu Ile Ser Gly Val Lys
1               5
```

```
<210> SEQ ID NO 4
<211> LENGTH: 11
<212> TYPE: PRT
<213> ORGANISM: Influenza virus
<220> FEATURE:
<221> NAME/KEY: MISC_FEATURE
<223> OTHER INFORMATION: fragment of conservative region of HB subtype

<400> SEQUENCE: 4

Asn Leu Asn Ser Leu Ser Glu Leu Glu Val Lys
1               5                   10

<210> SEQ ID NO 5
<211> LENGTH: 7
<212> TYPE: PRT
<213> ORGANISM: Bordetella pertussis
<220> FEATURE:
<221> NAME/KEY: MISC_FEATURE
<223> OTHER INFORMATION: fragment of pertussis toxin induced by trypsin
      cleavage

<400> SEQUENCE: 5

Ile Pro Pro Glu Asn Ile Arg
1               5

<210> SEQ ID NO 6
<211> LENGTH: 11
<212> TYPE: PRT
<213> ORGANISM: Bordetella pertussis
<220> FEATURE:
<221> NAME/KEY: MISC_FEATURE
<223> OTHER INFORMATION: fragment of pertussis toxin induced by trypsin
      cleavage

<400> SEQUENCE: 6

Ser Val Ala Ser Ile Val Gly Thr Leu Val Arg
1               5                   10

<210> SEQ ID NO 7
<211> LENGTH: 12
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 7

Ile Val Leu Leu Phe Ala Ile Val Ser Leu Val Lys
1               5                   10

<210> SEQ ID NO 8
<211> LENGTH: 23
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 8

Ser Asp Gln Ile Cys Ile Gly Tyr His Ala Asn Asn Ser Thr Glu Gln
1               5                   10                  15

Val Asp Thr Ile Met Glu Lys
            20

<210> SEQ ID NO 9
<211> LENGTH: 13
```

```
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 9

Asn Val Thr Val Thr His Ala Gln Asp Ile Leu Glu Lys
1               5

```
<211> LENGTH: 5
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 14

His Leu Leu Ser Arg
1               5

<210> SEQ ID NO 15
<211> LENGTH: 6
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 15

Ile Asn His Phe Glu Lys
1               5

<210> SEQ ID NO 16
<211> LENGTH: 6
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 16

Ile Gln Ile Ile Pro Lys
1               5

<210> SEQ ID NO 17
<211> LENGTH: 21
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 17

Ser Ser Trp Ser Ser His Glu Ala Ser Leu Gly Val Ser Ser Ala Cys
1               5                   10                  15

Pro Tyr Gln Gly Lys
            20

<210> SEQ ID NO 18
<211> LENGTH: 5
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 18

Ser Ser Phe Phe Arg
1               5

<210> SEQ ID NO 19
<211> LENGTH: 7
<212> TYPE: PRT
```

```
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 19

Asn Val Val Trp Leu Ile Lys
1               5

<210> SEQ ID NO 20
<211> LENGTH: 8
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 20

Asn Ser Thr Tyr Pro Thr Ile Lys
1               5

<210> SEQ ID NO 21
<211> LENGTH: 27
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 21

Ser Tyr Asn Asn Thr Asn Gln Glu Asp Leu Leu Val Leu Trp Gly Ile
1               5                   10                  15

His His Pro Asn Asp Ala Ala Glu Gln Thr Lys
            20                  25

<210> SEQ ID NO 22
<211> LENGTH: 19
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 22

Leu Tyr Gln Asn Pro Thr Thr Tyr Ile Ser Val Gly Thr Ser Thr Leu
1               5                   10                  15

Asn Gln Arg

<210> SEQ ID NO 23
<211> LENGTH: 4
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 23

Leu Val Pro Arg
1

<210> SEQ ID NO 24
<211> LENGTH: 4
<212> TYPE: PRT
```

```
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 24

Ile Ala Thr Arg
1

<210> SEQ ID NO 25
<211> LENGTH: 7
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 25

Val Asn Gly Gln Ser Gly Arg
1               5

<210> SEQ ID NO 26
<211> LENGTH: 30
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 26

Met Glu Phe Phe Trp Thr Ile Leu Lys Pro Asn Asp Ala Ile Asn Phe
1               5                   10                  15

Glu Ser Asn Gly Asn Phe Ile Ala Pro Glu Tyr Ala Tyr Lys
            20                  25                  30

<210> SEQ ID NO 27
<211> LENGTH: 7
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 27

Gly Asp Ser Thr Ile Met Lys
1               5

<210> SEQ ID NO 28
<211> LENGTH: 11
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 28

Ser Glu Leu Glu Tyr Gly Asn Cys Asn Thr Lys
1               5                   10

<210> SEQ ID NO 29
<211> LENGTH: 27
<212> TYPE: PRT
<213> ORGANISM: Influenza virus
<220> FEATURE:
```

```
<221> NAME/KEY: MISC_FEATURE
<223> OTHER INFORMATION: fragment of HA subtype by in silico trypsin
      cleavage

<400> SEQUENCE: 29

Cys Gln Thr Pro Met Gly Ala Ile Asn Ser Ser Met Pro Phe His Asn
1               5                   10                  15

Ile His Pro Leu Thr Ile Gly Glu Cys Pro Lys
            20                  25

<210> SEQ ID NO 30
<211> LENGTH: 8
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 30

Leu Val Leu Ala Thr Gly Leu Arg
1               5

<210> SEQ ID NO 31
<211> LENGTH: 38
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 31

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30

Gly Tyr Ala Ala Asp Lys
        35

<210> SEQ ID NO 32
<211> LENGTH: 5
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 32

Glu Ser Thr Gln Lys
1               5

<210> SEQ ID NO 33
<211> LENGTH: 8
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 33

Ala Ile Asp Gly Val Thr Asn Lys
1               5

<210> SEQ ID NO 34
```

```
<211> LENGTH: 7
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 34

Val Asn Ser Ile Ile Asp Lys
1               5

<210> SEQ ID NO 35
<211> LENGTH: 10
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 35

Met Asn Thr Gln Phe Glu Ala Val Gly Arg
1               5                   10

<210> SEQ ID NO 36
<211> LENGTH: 7
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 36

Glu Phe Asn Asn Leu Glu Arg
1               5

<210> SEQ ID NO 37
<211> LENGTH: 6
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 37

Ile Glu Asn Leu Asn Lys
1               5

<210> SEQ ID NO 38
<211> LENGTH: 23
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 38

Met Glu Asp Gly Phe Leu Asp Val Trp Thr Tyr Asn Ala Glu Leu Leu
1               5                   10                  15

Val Leu Met Glu Asn Glu Arg
            20

<210> SEQ ID NO 39
<211> LENGTH: 10
<212> TYPE: PRT
```

```
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 39

Thr Leu Asp Phe His Asp Ser Asn Val Lys
1               5                   10

<210> SEQ ID NO 40
<211> LENGTH: 5
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 40

Asn Leu Tyr Asp Lys
1               5

<210> SEQ ID NO 41
<211> LENGTH: 4
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 41

Leu Gln Leu Arg
1

<210> SEQ ID NO 42
<211> LENGTH: 4
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 42

Asp Asn Ala Lys
1

<210> SEQ ID NO 43
<211> LENGTH: 12
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 43

Glu Leu Gly Asn Gly Cys Phe Glu Phe Tyr His Lys
1               5                   10

<210> SEQ ID NO 44
<211> LENGTH: 10
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage
```

<400> SEQUENCE: 44

Cys Asp Asn Glu Cys Met Glu Ser Val Arg
1               5                   10

<210> SEQ ID NO 45
<211> LENGTH: 14
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 45

Asn Gly Thr Tyr Asp Tyr Pro Gln Tyr Ser Glu Glu Ala Arg
1               5                   10

<210> SEQ ID NO 46
<211> LENGTH: 42
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 46

Leu Glu Ser Ile Gly Ile Tyr Gln Ile Leu Ser Ile Tyr Ser Thr Val
1               5                   10                  15

Ala Ser Ser Leu Ala Leu Ala Ile Met Val Ala Gly Leu Ser Leu Trp
            20                  25                  30

Met Cys Ser Asn Gly Ser Leu Gln Cys Arg
        35                  40

<210> SEQ ID NO 47
<211> LENGTH: 12
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 47

Ile Val Leu Leu Phe Ala Ile Val Ser Leu Val Lys
1               5                   10

<210> SEQ ID NO 48
<211> LENGTH: 13
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 48

Asn Val Thr Val Thr His Ala Gln Asp Ile Leu Glu Lys
1               5                   10

<210> SEQ ID NO 49
<211> LENGTH: 13
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin cleavage

<400> SEQUENCE: 49

Leu Cys Asp Leu Asp Gly Val Lys Pro Leu Ile Leu Arg
1               5                   10

<210> SEQ ID NO 50
<211> LENGTH: 6
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 50

Ile Asn His Phe Glu Lys
1               5

<210> SEQ ID NO 51
<211> LENGTH: 6
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 51

Ile Gln Ile Ile Pro Lys
1               5

<210> SEQ ID NO 52
<211> LENGTH: 5
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 52

Ser Ser Phe Phe Arg
1               5

<210> SEQ ID NO 53
<211> LENGTH: 7
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 53

Asn Val Val Trp Leu Ile Lys
1               5

<210> SEQ ID NO 54
<211> LENGTH: 7
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 54

Val Asn Gly Gln Ser Gly Arg

<210> SEQ ID NO 55
<211> LENGTH: 8
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 55

Leu Val Leu Ala Thr Gly Leu Arg
1               5

<210> SEQ ID NO 56
<211> LENGTH: 5
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 56

Asn Ser Pro Gln Arg
1               5

<210> SEQ ID NO 57
<211> LENGTH: 5
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 57

Glu Ser Thr Gln Lys
1               5

<210> SEQ ID NO 58
<211> LENGTH: 8
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 58

Ala Ile Asp Gly Val Thr Asn Lys
1               5

<210> SEQ ID NO 59
<211> LENGTH: 7
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 59

Val Asn Ser Ile Ile Asp Lys
1               5

<210> SEQ ID NO 60
<211> LENGTH: 7

```
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 60

Glu Phe Asn Asn Leu Glu Arg
1               5

<210> SEQ ID NO 61
<211> LENGTH: 6
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 61

Ile Glu Asn Leu Asn Lys
1               5

<210> SEQ ID NO 62
<211> LENGTH: 10
<212> TYPE: PRT
<213> ORGANISM: Influenza virus
<220> FEATURE:
<221> NAME/KEY: MISC_FEATURE
<223> OTHER INFORMATION: fragment of HA subtype by in silico trypsin
      cleavage

<400> SEQUENCE: 62

Thr Leu Asp Phe His Asp Ser Asn Val Lys
1               5                   10

<210> SEQ ID NO 63
<211> LENGTH: 11
<212> TYPE: PRT
<213> ORGANISM: Artificial Sequence
<220> FEATURE:
<223> OTHER INFORMATION: isotope enriched Phe 9 residue to change
      molecular weight relative to SEQ ID NO: 1
<220> FEATURE:
<221> NAME/KEY: MOD_RES
<222> LOCATION: (1)..(1)

<400> SEQUENCE: 63

Glu Gln Leu Ser Ser Val Ser Ser Phe Glu Arg
1               5                   10

<210> SEQ ID NO 64
<211> LENGTH: 12
<212> TYPE: PRT
<213> ORGANISM: Artificial Sequence
<220> FEATURE:
<223> OTHER INFORMATION: isotope enriched Ile 9 residue to change
      molecular weight relative to SEQ ID NO: 2
<220> FEATURE:
<221> NAME/KEY: MOD_RES
<222> LOCATION: (1)..(1)

<400> SEQUENCE: 64

Ser Thr Gln Ala Ala Ile Asn Gln Ile Asn Gly Lys
1               5                   10

<210> SEQ ID NO 65
<211> LENGTH: 7
<212> TYPE: PRT
```

```
<213> ORGANISM: Artificial Sequence
<220> FEATURE:
<223> OTHER INFORMATION: isotope enriched Val 6 residue to change
      molecular weight relative to SEQ ID NO: 3
<220> FEATURE:
<221> NAME/KEY: MOD_RES
<222> LOCATION: (1)..(1)

<400> SEQUENCE: 65

Glu Glu Ile Ser Gly Val Lys
1               5

<210> SEQ ID NO 66
<211> LENGTH: 11
<212> TYPE: PRT
<213> ORGANISM: Artificial Sequence
<220> FEATURE:
<223> OTHER INFORMATION: isotope enriched Leu 8 residue to change
      molecular weight relative to SEQ ID NO: 4
<220> FEATURE:
<221> NAME/KEY: MOD_RES
<222> LOCATION: (1)..(1)

<400> SEQUENCE: 66

Asn Leu Asn Ser Leu Ser Glu Leu Glu Val Lys
1               5                   10
```

VIRAL PROTEIN QUANTIFICATION PROCESS AND VACCINE QUALITY CONTROL THEREWITH

RELATED APPLICATIONS

This application is the U.S. national phase of PCT/US2008/013396 filed Dec. 5, 2008, which claims priority benefit of U.S. Provisional Application 60/992,520 filed Dec. 5, 2007, the contents of which are incorporated herein by reference.

FIELD OF THE INVENTION

The present invention relates to a process for the quantification of a viral protein by a liquid chromatography mass spectrometry assay, when present in a composition and in particular for accurate and rapid detection of viral hemagglutinins in influenza vaccine growth media in order to quantify rapidly viral load during influenza vaccine production.

BACKGROUND OF THE INVENTION

Developing annual vaccine strategies for reducing the severity and prevalence of influenza outbreaks presently requires vigilant monitoring of currently circulating viral strains. This is due to the rapid mutational rate of the protective hemagglutinin (HA) and neuraminidase on the viral surface. Antibodies raised to prior hemagglutinin and neuraminidase sequences will not confer protection from a newly emerged form. Indeed, a single point mutation might render a vaccine inactive toward the new viral mutant form. Alymova, I C, et al, *J Virol,* 1998; 72:4472-77; Kodihelli, S, et al, *J Virol,* 1995; 69:4888-97 Moreover, carefully updated and current data on currently circulating strains the choice of which strains to include in the following season's vaccine must be made six months or more in advance.

The primary source of delay from decision to vaccine delivery is due to quantification of protective hemagglutinin (HA) during the production cycle. Currently, HA is quantified by a single radial immunodiffusion (SRID) assay employing standardized antigens and specific sheep antiserum, and quantified by densitometry of active bands separated by gel electrophoresis. Schild G C, et al., *Bull World Health Organ,* 1975; 52:223-31; Wood, J, et al, *Dev Biol Stand,* 1977; 39:193-200. The SRID assay is performed by solubilization of the target viral complex and immunodiffusion of the HA through an agarose gel containing antibodies specific for the HA sequence. HA is quantified by precipitation in the region of immunocomplex formation, the size of which is directly proportional to the amount of HA present in the solution. By comparison to a standard curve of known HA concentration produced by the standardized antigens the amount of a specific subtype of HA is determined. Wood, J M, et al, *J Biol Stand,* 1977; 5:237-247; Williams, M S, *Vet Microbiol,* 1993; 37:253-26. However, generation of calibrated reagents such as specific antiserum to the target viral antigen requires at least two-three months. Thus, a large portion of the time required to bring a vaccine to market is devoted to the single step of quantifying viral antigen during the production process. Further, the SRID assay is sensitive to matrix ionic strength and pH reducing the assay's overall accuracy. Willkommen, H., et al, *Acta Virol,* 1983; 27:407-11. This requirement for specific antiserum to the target viral antigen frustrates vaccine development to other rapidly mutating viruses such as HIV and avian influenza.

The World Health Organization constantly monitors the prevalence of individual influenza strains throughout the world in an effort to predict which strains will be most prevalent in the following year. This information is used to determine which influenza strains to include in the next round of vaccine production. However, the time from decision to the vaccine reaching market can be six months or more. During this time a particular strain may have mutated rendering the produced vaccine inactive and reducing the overall effectiveness of the entire influenza vaccine program. Also, in the event that a viral strain mutates to become highly infective producing severe symptoms, a pandemic situation may occur that the current vaccine program will be unable to adequately respond to due to the minimum of several months from identification of the strain until the first vaccine is available.

A primary source of the delay in vaccine production is in obtaining rapid and accurate quantification of immunogenic antigens, and hence viral concentrations in the vaccine under production. The long time from viral identification to market delivery would be devastating in the event of an influenza pandemic. Thus, it is essential that new methods be developed to shorten production time. Recently, quantitative analysis of hemagglutinin antigen by high performance liquid chromatography (HPLC) was reported. Kapteyn, J C, et al, *Vaccine,* 2006; 24:3137-44; Garcia-Canas, V, et al, *Anal Chem,* 2007; 79:3164-72. This assay method capitalizes on trypsin cleavage of HA into $HA_1$ and $HA_2$ strands linked by a single disulfide bond. Simple reduction of this bond allows separation of the $HA_1$ strand from the remainder of the viral components by HPLC. The amount of $HA_1$ is determined by measurement of peak area and comparison to that of a standard curve of known quantified $HA_1$ antigen. However, the amount of standard $HA_1$ antigen must be first determined by the traditional SCID assay. Thus, this assay fails to overcome the traditional SCID assay drawbacks of generating standard reagents and specific antibodies. Further, identification and quantification of three different HA subtypes from complex viral production media is not possible.

Other methods for rapidly identifying particular viral strains are presently being developed. Morrissey and colleagues report a matrix-assisted laser desorption/ionization (MALDI) method of generating a fingerprint of particular viral strains. Morrissey, B, et al, *J. Virol Meth,* 2007; 145:106-14. By identifying particular antigenic regions in HA1 and HA2, these investigators are able to rapidly monitor the prevalence of particular strains. While this method represents a step forward in determining which strains are to be included in the next round of vaccine production, it does not reduce the time required to produce vaccine.

Thus, there exists a need for an improved process of quantifying viral proteins in the vaccine production cycle. There further exists a need for quantifying viral proteins on a time scale that allows vaccine modification to confer protection against a newly emerging strain.

SUMMARY OF THE INVENTION

A process of quantifying a protein, which comprises: digesting a composition comprising the protein to obtain a second composition comprising at least one peptide; adding at least one standard peptide to the second composition to obtain a third composition; subjecting the third composition to a liquid chromatograph mass spectrometry (LCMS) assay to obtain a mass of at least one peptide and a mass of at least one standard peptide; and determining a mass ratio of at least one peptide to the mass of at least one standard peptide; and comparing the mass ratio to a calibration curve. In the instance that the protein is immunogenic, the process is advantageous in that quantitation may be realized without the need to produce standardized antibodies.

BRIEF DESCRIPTION OF THE DRAWINGS

FIG. 4 represents quantitative results from replicate injections of 20 digest preparations;

Figure 8:
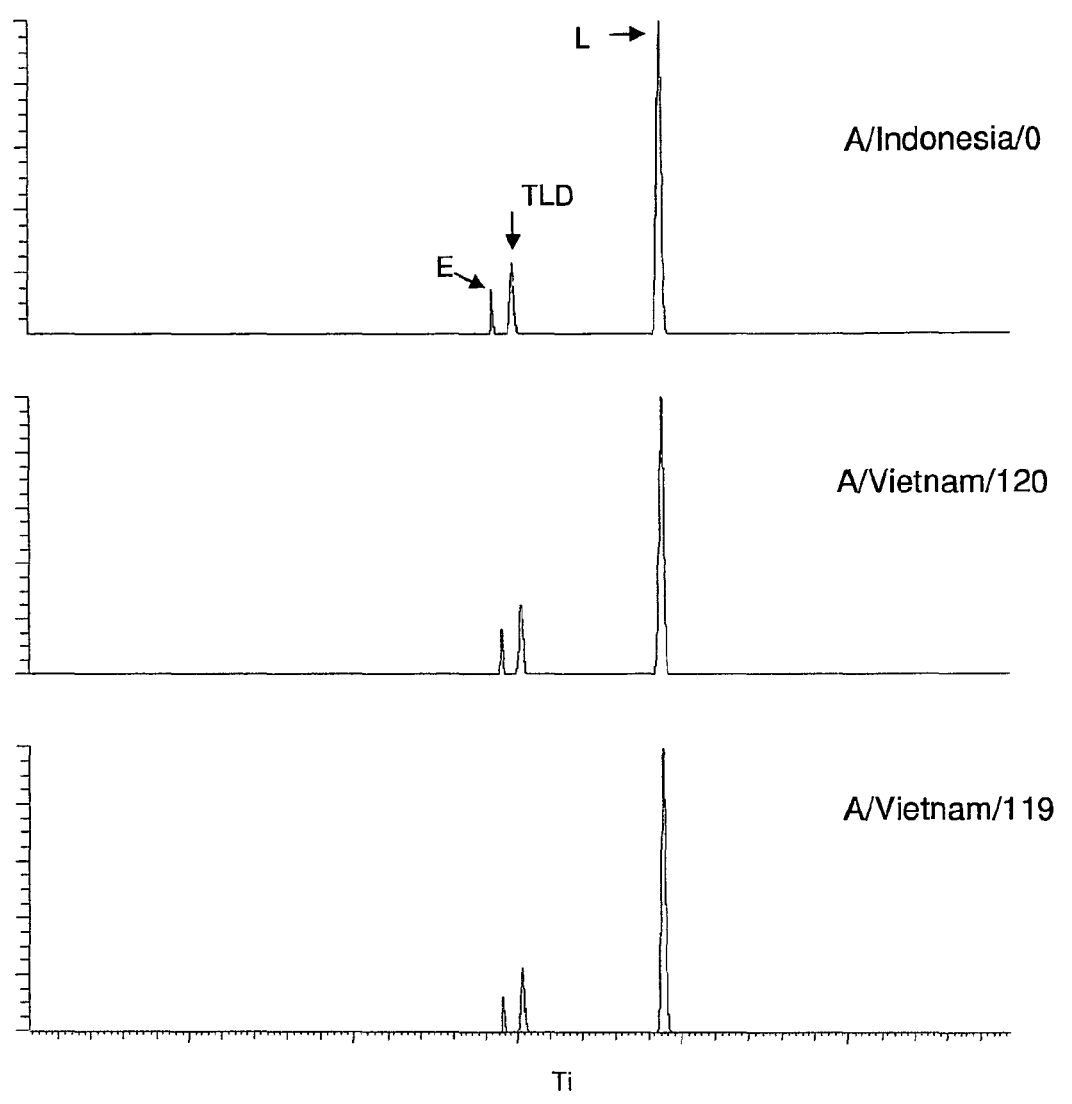

FIG. 8 is a multiple reaction monitoring liquid chromatograms of purified H5N1 virions using three conserved showing the selectivity of the LC-MRM method for all three targeted peptides; and FIG. 9 are multiple reaction monitoring (LC-MRM) chromatograms of three hemagglutinin components of seasonal influenza vaccine for the influenza suybtypes so labelled.

DETAILED DESCRIPTION OF THE PREFERRED EMBODIMENTS

The present invention has utility as a rapid and accurate process for quantifying multiple viral strains in a complex mixture. Particularly, the instant invention has utility for rapidly distinguishing and quantifying immunogenic influenza surface antigens without the need for producing standardized antibodies and as a result finds particular utility in commercial vaccine production. The present invention provides a process of quantifying an immunogencity indicative of subjecting a composition containing at least one immunogenic protein fragmented peptide and at least one standard peptide to a liquid chromatograph mass spectrometry (LCMS) assay to obtain a mass of at least one immunogencity and a mass of at least one standard peptide; and determining a mass ratio obtained by dividing the mass of at least one immunogencity and the mass of at least one standard peptide; and comparing the mass ratio to a calibration curve to determine the degree of immunogencity of the composition. When the composition is a vaccine, the protective nature is assessed. With the lipid determination of the present invention, composition content is adjusted to mass produce effective vaccine.

Another embodiment is directed to a process of quantifying a protein, which comprises: digesting a composition comprising the protein to obtain a second composition comprising at least one peptide; adding at least one standard peptide to the second composition to obtain a third composition; subjecting the third composition to a liquid chromatograph mass spectrometry (LCMS) assay to obtain a mass of at least one peptide and a mass of at least one standard peptide; and determining a mass ratio of at least one peptide to the mass of at least one standard peptide; and comparing the mass ratio to a calibration curve.

Yet another embodiment is directed to a process of quantifying a protein, which comprises: subjecting a composition comprising at least one peptide and at least one standard peptide to a liquid chromatography mass spectrometry (LCMS) assay to obtain a mass of at least one peptide and a mass of at least one standard peptide; and determining a mass ratio obtained by dividing the mass of at least one peptide and the mass of at least one standard peptide; and comparing the mass ratio to a calibration curve.

An additional embodiment is directed to a method of preparing an influenza vaccine, which comprises: identifying at least one influenza virus strain comprising a protein; digesting a composition comprising the protein to obtain a second composition comprising at least one peptide; adding at least one standard peptide to the second composition to obtain a third composition; subjecting the third composition to a liquid chromatograph mass spectrometry (LCMS) assay to obtain a mass of at least one peptide and a mass of at least one standard peptide; and determining a mass ratio of at least one peptide to the mass of at least one standard peptide; and comparing the mass ratio to a calibration curve.

A method of vaccinating a patient in need thereof, which comprises: administering to the patient in need thereof a vaccine obtained by a process which comprises identifying at least one influenza virus strain comprising a protein; digesting a composition comprising the protein to obtain a second composition comprising at least one peptide; adding at least one standard peptide to the second composition to obtain a third composition; subjecting the third composition to a liquid chromatograph mass spectrometry (LCMS) assay to obtain a mass of at least one peptide and a mass of at least one standard peptide; and determining a mass ratio of at least one peptide to the mass of at least one standard peptide; and comparing the mass ratio to a calibration curve.

In a preferred embodiment, the instant invention provides a process for quantifying antigens in a complex mixture such as a solution. This inventive process is capable of quantifying 100 or more peptides from a single or multiple antigens in the complex solution. There is no upper limit on the number of peptides quantifiable in the instant invention as long as each peptide.

The present invention also provides a process of quantifying an immunogenic protein, including digesting a composition containing the protein to obtain a second composition containing at least one immunogenic protein fragment from the protein; adding at least one standard peptide to the second composition to obtain a third composition; subjecting the third composition to a liquid chromatograph mass spectrometry (LCMS) assay to obtain a mass of at least one immunogenic protein and a mass of at least one standard peptide; and determining a mass ratio obtained by dividing the mass of at least one immunogenic protein and the mass of at least one standard peptide; and comparing the mass ratio to a calibration curve.

The protein according to the present invention is a viral protein. Alternative sources of the protein illustrated include a bacterial protein, a protozoan protein, a fungal protein, a proteinaceous infectious particle (i.e., a prion), a glycoprotein, a lipoprotein, a glyco-lipo-protein, or a eukaryotic protein. Not to be limited by way of example, but a protein source includes one or more of the following *Escherichia coli, Mycobacterium tuberculosis, Bacillus anthracis, Salmonella, Staphylococcus aureus, Streptococcus pneumoniae, Haemophilus influenzae, Streptococcus pyogenes, Helicobacter pylori,*

Figure 1:
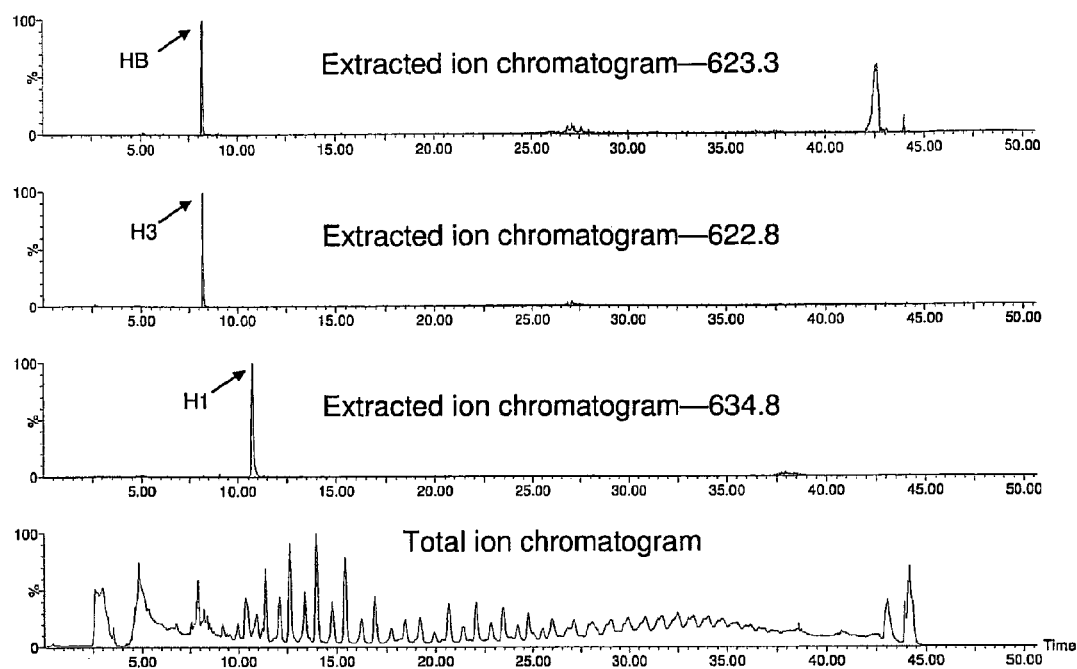
FIG. 1 represents a total ion chromatogram following liquid chromatography of a digested trivalent vaccine and extracted ion chromatograms for peptides from HB, H3, and H1, each components of the trivalent vaccine eluted in the total ion chromatogram.

*Francisella tularensis, Klebsiella pneumoniae, Bacillus anthracis, Burkholderia mallei, Burkholderia pseudomallei,* hepatitis A, hepatitis B, hepatitis C, hepatitis D, hepatitis E, herpes simplex virus, molluscum contagiosum virus, human immunodeficiency virus, influenza virus, *Cryptosporidium, Giardia lamblia, Plasmodium, Trypanosoma cruzi, Pneumocystis jirovecii, Tinea, Candida, Histoplasma capsulatum, Cryptococcus neoformans,* roundworm, and tapeworm.

Of particular public health and commercial importance is a protein obtained from a viral source selected from among an influenza virus; a paramyxovirus; a mumps virus; a rubella virus; a Flaviviridae virus, and a human immunodeficiency virus. It is understood that the Flaviviridae virus family comprises a Flavivirus, such as, a West Nile virus, a dengue virus, a tick-borne encephalitis Virus, and a yellow Fever Virus yellow fever virus; a Hepcivirus, such as, Hepatitis C virus; and a Pestivirus, such as, a Border disease virus, a Bovine virus diarrhea, and a classical swine fever virus.

Alternatively, the protein is obtained from a solution of commercial vaccine preparation, microorganisms in growth media or other suitable media, crude or purified peptides, nucleic acids, organic or inorganic polymers, vitamins, metabolites, lipids, or other suitable material. Preferably, the solution contains one or more viral or microorganism strains, species, or other genotypically or phenotypically unique life forms. Optionally, the solution contains a strain or strains of diphtheria (*Corynebacterium diphtheriae*), tetanus (*Clostridium tetani*), pertussis (*Bordetella pertussis*), hepatitis A, B, and C, *Streptococcus pneumoniae*, poliovirus illustratively including Types 1, 2, and 3, varicella virus, measles virus (Enders' attenuated Edmonston strain), mumps virus (the Jeryl Lynn (B level) strain), rubella virus (the Wistar RA 27/3 strain), *Haemophilus influenzae,* any organism or immunodeterminant thereof selected from among Acel-Imune, ActHIB, Animal Serum Products, Anthrax vaccine, Attenuvax, BCG see Tice BCG, USP, Biavax II, Botulinum toxin (Botox), Chickenpox vaccine (Varicella zoster vaccine), Cholera Vaccine, Comvax Sterile Suspension, Diphtheria and Tetanus Toxoids and Pertussis Vaccine Adsorbed (DTP), Diphtheria vaccine, Engerix-B Unit-Dose Vials, Flu vaccine (influenza), Fluvirin, Gamma globulin, Gammar, German measles (rubella) vaccine, Havrix, HBIG, Hepatitis A vaccine, Hepatitis B vaccine, Hep-B-Immune Globulin, Heptavax, HibTITER, Immune globulin see gamma globulin, Imovax Rabies Vaccine, Infanrix for Intramuscular Injection, Influenza Virus Vaccine (Flu), Ipol, Japanese Encephalitis Virus vaccine, JE-Vax, Liquid PedvaxHIB, Lyme Disease, Lyophilized PedvaxHIB, Measles vaccine see Rubella and Rubeola vaccines, Meningococcal polysaccharide vaccine, Menomune-A/C/Y/W-135, Meruvax II, M-M-R II, M-R-VAX II, Mumps vaccine, Mumpsvax, OmniHIB, Orimune, Paratyphoid vaccine, Pertussis vaccine, Plague vaccine, Pneumococcal vaccine, Pneumovax 23, Pnu-Imune 23, Polio (injectible) vaccine, Polio (oral) vaccine, Rabies Vaccine Adsorbed, Rabies Vaccine, Imovax Rabies I.D., Recombivax HB, RhoGAM, Rubeola vaccine, Smallpox vaccine, Tetanus vaccine, Tetramune, Tice BCG (USP), Tri-Immunol Adsorbed, Tripedia, Vaccine: Hepatitis B (Recombinant), and Vaccine: Rh Immune Globulin, cholera, rabies, Japanese encephalitis, yellow fever, typhoid, botulinum toxin, any strain of influenza illustratively including types A and B, combinations thereof, mutants thereof, or fragments thereof. In a more preferred embodiment, the protein is obtained from an influenza virus that comprises at least one of the hemagglutinin subtypes of H1, H3, H5, or HB; a neuraminidase, a nucleoprotein, or a matrix protein.

In a preferred embodiment, the protein is obtained from a production solution of one or more influenza strains. Although any suitable growth media is operable as a source of sample for use in the present invention, the commonly employed propagation media of embryonated chicken eggs is presently preferred. The present invention is operable independent of other components of the growth media illustratively including detergents, formaldehyde, surfactants, or buffered salt solutions.

The protein according to the present invention is digested optionally and with an endoprotease. Exemplary, specific endoproteases are tabulated in the Exemplary Endoproteases of Table 1. Preferably, the endoprotease is trypsin.

Preferably, the influenza strains are partially isolated from the growth media by techniques known in the art. Illustratively, a trivalent sample of influenza virus stored in phosphate buffered saline or ammonium bicarbonate is used as a sample source. The sample is preferably subjected to enzymatic digestion. Suitable enzymes for digestion are illustratively trypsin, chymotrypsin, endoproteinase Asp-N, endoproteinase Arg-C, endoproteinase Glu-C, endoproteinase Lys-C, pepsin, thermolysin, elastase, papain, proteinase K, subtilisin, clostripain, exopeptidase, carboxypeptidase A, B, P, or Y, cathepsin C, acylamino-acid-releasing enzyme, pyroglutamate aminopeptidase, other proteases illustrated in Table 1 combinations thereof, mutants thereof, or fragments thereof. *Cold Spring Harbor Protocols.* Proteases suitable for use in the instant invention are illustratively obtained from Sigma-Aldrich, Co. (St. Louis, Mo.). It is appreciated that other proteases are similarly suitable for use in the instant invention. Additionally, it is appreciated that other chemical means of digestion are suitable illustratively including, acid, base, or other chemical digestion methods known in the art.

TABLE 1

| Exemplary Endoproteases |
|---|
| Achromopeptidase |
| Aminopeptidase |
| Angiotensin Converting Enzyme |
| Bromelain |
| Calpain I |
| Carboxypeptidase A |
| Carboxypeptidase B |
| Carboxypeptidase G |
| Carboxypeptidase P |
| Carboxypeptidase W |
| Carboxypeptidase Y |
| Caspase 1 |
| Caspase 10 |
| Caspase 2 |
| Caspase 3 |
| Caspase 4 |
| Caspase 5 |
| Caspase 6 |
| Caspase 7 |
| Caspase 8 |
| Caspase 9 |
| Cathepsin B |
| Cathepsin C |
| Cathepsin D |
| Cathepsin G |
| Cathepsin H |
| Cathepsin L |
| Chymase |
| Chymopapain |
| Chymotrypsin, alpha |
| Clostripain |
| Cucumisin |
| Dipeptidyl peptidase IV |
| Elastase, leukocyte |
| Elastase, pancreatic |

TABLE 1-continued

Exemplary Endoproteases

Endoproteinase Arg-C
Endoproteinase Asp-N
Endoproteinase Glu-C
Endoproteinase Lys-C
Enterokinase
Factor Xa
Ficin
Furin
Granzyme B
HIV Protease
Igase
Kallikrein tissue
Leucine aminopeptidase, microsomal
Matrix metalloproteinase-7
Matrix metalloproteinase-9
Methionine Aminopeptidase
Papain
Pepsin
Plasmin
Prolidase
Pronase E
Prostate Specific Antigen
Proteinase 3
Pyroglutamate aminopeptidase
Renin
Rennin
Streptokinase
Subtilisin
Thermolysin
Thrombin
Tissue Plasminogen Activator
Trypsin
Tryptase
Urokinase The resulting fragments of digestion are then analyzed by a suitable, rapid, and quantitative analysis technique. Preferably, analysis is performed by liquid chromatography (LC) coupled to mass spectrometry (MS). LC techniques suitable for use in the present invention, include but are not limited to, high-performance LC, ultra-high performance LC, and standard column or slab gel chromatography techniques. Examples of suitable columns for separation of digestion products (target peptides) illustratively include a $C_{18}$ HPLC column such as the Symmetery-300 $C_{18}$ column available from Waters, Corp. (Bedford, Mass.). It is appreciated that other column types are similarly suitable for use in the present invention. Column parameters such as inner diameter, length, number of theoretical plates, etc. are recognized in the art and persons having ordinary skill in the art readily recognize methods of optimizing these and other necessary parameters to facilitate effective separation of a single or family of target peptides. Thus, it does not require undue experimentation to adjust parameters of LC columns.

A second or other additional columns are optionally employed to further separate the target peptides. In a preferred embodiment, the elution of a $C_{18}$ reverse phase HPLC column is coupled to a chromatographic step on a Waters NanoAcquity column also available from Waters, Corp. The separated target peptides are subsequently submitted to a mass spectrometry system for detection, identification, and quantitation.

The protein is optionally digested with an endoprotease in presence of a surfactant. The surfactant may comprise a nonionic surfactant, a cationic surfactant, an anionic surfactant, a zwitterion surfactant, or combinations thereof. Examples of surfactants are disclosed in U.S. Published Application No. 2006/0078609 (U.S. patent application Ser. No. 10/536,542) and specifically including those found at page 2, para. [0025] to page 4, para. [0048]. Other examples of surfactants are disclosed in U.S. Pat. No. 6,294,192 and those specifically disclosed at column 5, line 9 to column 19, line 53. As exemplified herein, a suitable surfactant comprises an acid liable detergent, such as, RAPIGEST (Waters, Bedford, Mass.).

The protein is optionally digested with an endoprotease in an aqueous solution including an inorganic or organic acid. Not to be limited by way of example, but an inorganic acid is an acid selected from among nitric acid, phosphoric acid, sulfuric acid, ammonium chloride, ammonium bicarbonate, etc., salts thereof, and combinations thereof. An organic acid is an acid selected from among oxalic acid, malonic acid, tartaric acid, acetic acid, formic acid, lactic acid, propionic acid, phthalic acid, benzoic acid, citric acid, succinic acid, salts thereof, and combinations thereof. The identity of the acid is not critical, but is intended only to facilitate the protein digestion, sample analysis, sample chromatography, ion detection, sample preparation, etc. In a preferred embodiment, the acid is formic acid or acetic acid having a concentration sufficient to maintain a pH value. The pH of the protein/endonuclease composition ranges from about 1.5 to about 7.0.

Optionally, the LCMS assay is a liquid chromatograph isotope dilution mass spectrometry assay or an ultra performance liquid chromatograph isotope dilution tandem mass spectrometry assay. It will be understood, by way of example below, that the LCMS assay further comprises a second stage mass spectrometry fragmentation analysis.

In a preferred embodiment, an inventive process provides for fragmenting the at least one peptide and the at least one standard peptide and measuring the masses of the fragments the at least one peptide to the masses of the fragments of the at least one standard peptide. More preferably, the fragmenting also includes the at least one peptide and the at least one standard peptide being fragmented into their respective amino acid components. In other words, the at least one peptide is fragmented into its individual amino acid components and the at least one standard peptide is fragmented into its individual amino acid components.

Suitable detection and quantitation systems illustratively include electrospray, matrix assisted laser desorbtion ionization (MALDI), time of flight (TOF), multiple quadropole, and other types of mass spectrometry systems known in the art. Illustratively, a Waters Q-T of Premier TOF quadrupole tandem mass spectrometer available from Waters, Corp. or an API 4000-Q trap triple quadrupole tandem mass spectrometer (Applied Biosystems, Foster City, Calif.) are each suitable for use in the present invention. It is appreciated that other brands and types of mass spectrometers are similarly suitable.

In a preferred embodiment a quadrupole time of flight mass spectrometer is used with detection by multiple reaction monitoring (MRM). MRM increases both the selectivity and the sensitivity of detection system by monitoring chromatographic co-elution of multiple transitions for a given peptide. Wolf-Yadlin, A, et al, *Proc Natl Acad Sci USA*, 2007; 104: 5860-65. MRM has been previously used for detection of doping substances (Guan, F, et al, *J Chromatogr B Analyt Technol Biomed Life Sci*, 2005; 829:56-68; Ho, E N, et al, *J Chromatogr A*, 2006; 1120:38-53; Thevis, M, et al, *Biomed Chromatogr*, 2001; 15:393-402; Herrin, G L, et al, *J Anal Toxicol*, 2005; 29:599-606), detection of DNA adducts (Koc, H & Swenberg, J A, *J Chromatogr B Analyt Technol Biomed Life Sci*, 2002; 778:323-343), and for some proteomic studies (Wolf-Yadlin, A, et al, *Proc. Nat. Acad. Sci, USA*, 2007; 104:5860-65; Kirkpatrick, D S, et al, *Methods*, 2005; 35:265-273; Liao, H, et al, *Arthritis Rheum*, 2004; 50:3792-3803).

It is appreciated that digesting the protein produces at least one immunogenic protein fragment peptide. It is understood that a peptide inherently has a certain amino acid sequence. Preferably, the amino acid sequence of the at least one immunogenic protein fragment peptide and the at least one standard peptide are the same. However, in order to quantify the amount of protein, in a sample that contains multiple proteins, it is critical that the mass of the at least one immunogenic protein fragment peptide and the mass of the at least one standard peptide are not the same. This aspect of the invention can be better understood by way of example, several of which are disclosed herein. However, in order to achieve a mass differential between the at least one immunogenic protein fragment peptide and the mass of the at least one standard peptide, it is preferred that the at least one standard peptide comprises at least one isotopically-enriched amino acid. For example, it is preferred that the at least one isotopically-enriched amino acid contains at least one isotope selected from among $^2H$, $^{13}C$, $^{15}N$, $^{17}O$, $^{18}O$, $^{33}S$, and $^{34}S$.

In a preferred embodiment, the at least one isotopically-enriched amino acid contains at least one isotope selected from among $^{13}C$ and $^{15}N$. For example, in the case of an amino acid sequence that has an amino acid, such as, phenylalanine, all of the carbons can be isotopically-enriched so as to comprise substantially $^{13}C$. An isotopically-enriched phenylalanine having substantially $^{13}C$ possesses a mass differential of about 9 when compared to non-isotopically-enriched phenylalanine. An additional mass differential is realized by utilizing an amino acid comprising both $^{13}C$ and $^{15}N$. Indeed, for the case of phenylalanine the mass differential between an isotopically-enriched phenylalanine having substantially $^{13}C$ and $^{15}N$ a non-isotopically-enriched phenylalaine is about 10.

It can be understood by the skilled artisan that isotopic enrichment is not the only means for obtaining a mass differential between the at least one peptide and the mass of the at least one standard peptide. For example, suitable mass labels incorporated into the at least one standard peptide include, but are not limited to, fluorine, a fluorescent label, such as rhodamine, Oregon green or others known in the art, radioactive labels, mass labels as disclosed in U.S. Pat. No. 6,649,354, and those disclosed in U.S. Pat. Nos. 6,635,452 and 7,132,519.

A calibration curve is optionally used and represents a mathematical relationship between a known amount of at least one immunogenic antigen fragment peptide and a ratio; wherein the ratio is the quotient of the known amount of the at least one peptide and a constant amount of at least one standard peptide.

Simultaneous with or subsequent to identification and detection in a suitable detector, the amount of target peptide is quantified with reference to a standard peptide. Standard peptides are illustratively mass labeled peptide(s) with amino acid sequence representative of the particular target peptide. In a non-limiting example, an illustrative peptide has the sequence EQLSSVSSFER(SEQ ID NO 1) and is derived from influenza subtype H1. Other illustrated peptides include, but are not limited to, peptides identified by SEQ ID NOs 2-4. Standard peptides or sample target peptides are illustratively synthesized by Sigma Genosys (The Woodlands, Tex.). From the amino acid sequence it is appreciated that this exemplary peptide has an observed mass to charge or 634.8 $(M+2H)^{2+}$. (FIG. 1) An exemplary standard peptide designed to serve as a quantitative standard for target peptide SEQ ID NO 1 has the sequence EQLSSVSSFER SEQ ID NO 63 with the phenylalanine incorporating $^{13}\overline{C}$ and $^{15}N$ to give the peptide a 10 kDa heavier peptide. As is observed in FIG. 2, this produces an observable mass of 639.8 $(M+2H)^{2+}$.

Quantitating the target peptide is optionally performed by techniques known in the art. In a non-limiting example, in the detection system of LC-IDT-MS/MS the mass labeled standard peptide is spiked into the test solution at a known concentration. In MRM each respective transition is composed of the monoisotopic precursor m/z and a selected monoisotopic product ion. Four transitional pairs are illustratively analyzed and the values for the target peptide are compared to the values of the standard peptide at known concentration to calculate the amount of target peptide in the respective digestion.

It is appreciated that the sequence of the standard peptide is representative of the target immunogenic protein fragment peptide. In the case of a newly arising mutation in the amino acid sequence, nucleotide sequence, or other, techniques for identification of the newly arising sequence, characterization of such, and isolation of representative target peptides representative of the newly arising sequence are well known in the art. Thus, the present method is not limited to use on the sequences explicitly illustrated herein. For example, the MALDI-MS technique described by Morrissey provides a simple, single-step determination of primary sequence and antigenicity of viral or other surface antigens. Morrissey, B., et al, *J Virol Meth*, 2007; 145:106-114. This technique is suitable for rapid monitoring of the emergence of new infective strains and characterization of its corresponding protein sequences.

Preferably, and to most rapidly improve decisions in time to adjust vaccine production, at least three conserved immunogenic protein fragment peptides of each known strain are synthesized in advance and stored until needed. However, if a strain mutates, characterization of the new mutation is straightforward and well established in the art. One or more standard peptides are synthesized in a matter of hours and less than a day away to the comparatively short length, and will, thus, be immediately suitable for use in quantization of viral protein during emergency vaccine production. Accordingly, it is immaterial that all possible sequences of viral or other proteins be known for a person of ordinary skill in the art to readily practice the present invention.

A target peptide is digested to a length of between 5 and 80 amino acid residues, and preferably between 7 and 20 residues. Selection of a target protein fragment peptide from a viral or other organism protein sequence is preferably directed to peptides with sequences that are highly conserved within the strain. In a non-limiting example, the peptide sequence EEISGVK (SEQ ID NO 3) is present at the C-terminus of the H5N1 strain A/Vietnam/1203/2004. The C-terminal region of H5N1 is highly conserved and sequence EEISGVK (SEQ ID NO 3) was 100% conserved in 91% of the strains present in the NCBI database as of February, 2007. H3 target peptide STQAAINQINGK (SEQ ID NO 2) was present in 69% of strains analyzed. A small nucleotide polymorphism (SNP) was found in 485 additional strains. HB target peptide NLNSLSELEVK (SEQ ID NO 4) was present in 98% of the strains analyzed. However, the sequence of each strain is readily ascertained or previously known. It is appreciated that other peptide sequences in this strain, as well as other strains, from other proteins, and from other organisms are similarly operable in the instant invention. It is further appreciated that a high degree of conservation in the target peptide is not required for practice of the instant invention as any given strain is subject to an extremely low mutational rate during vaccine production. Thus, a simple characterization of a particular peptide region is all that is necessary to use a selected target peptide in the present process.

Preferably, the selected target protein fragment peptide displays high to noise of at least 6 and preferably at least 11 signal intensity in the selected detection and quantitation system. Further, it is preferred that a target peptide display a lack of missed cleavages, absence of split charge states, and an absence of methionine and tryptophan as these residues are commonly oxidized in vivo and during handling. Testing a family of peptides produced in a digest of a target protein for the above parameters is both rapid and well within the skill of an ordinary practitioner in the art. For example, only a few hours are required to prepare a set of control samples, subject them to digestion and experimentally determine the most favorable protein fragment peptides for use in quantitation of virus during vaccine production. Thus, undue experimentation is not required to determine suitable target peptides from any existing viral or other organism strain or emerging strains.

In a preferred embodiment the sample is an influenza sample solution. The instant invention does not require any particular strain of influenza. Numerous strains are operable illustratively including strains with HA subtypes H1, H2, H3, H4 H5, H6, H7, H8, H9, H10, H11, H12, H13, H14, H15, H16, and HB. It is appreciated that this is an inclusive list and not exclusive of other strains or other HA subtypes that are similarly operable.

Other proteins are present on the influenza surface suitable for use in the present process, which include, but are not limited to, hemagglutinin, and neuraminidase. Further, other proteins are similarly suitable for use in the present process depending on the selected organism for which a vaccine or therapy is being produced illustratively including nucleoprotein, matrix protein, HBsAg, HBcAg, antigens described in U.S. Published Applications 2003/0202982 and 2007/0036826, gp120 protein, outer surface protein A as disclosed in U.S. Pat. No. 5,683,702, antigens as illustrated in U.S. Pat. No. 6,627,202, combinations thereof, and fragments thereof.

Preferably, the selected protein used as a sample for generating target peptides by digestion is immunogenic in nature. More preferably, the selected protein is an immunogenic viral protein. Most preferably, the protein is an influenza HA or HB subtype.

According to the present invention, one obtains a sample, subjects the sample to digestion, measures the amount of at least one target protein fragment peptide within the digested sample by an LC/MS method, and quantifies the amount of target peptide to correlate with and quantify the amount of sample protein. Moreover, by determining the amino acid sequence of a selected protein within a sample or a portion thereof, and obtaining a standard peptide with an amino acid sequence representative of the amino acid sequence of the selected protein or portion thereof.

Determining the amino acid sequence of a selected protein within a sample or portion thereof is performed by techniques well known and established in the art. In a family of non-limiting examples, simple gel electrophoresis combined with mass spectrometry, or mass spectrometry techniques alone have been widely used for sequencing of the proteome from many organisms and tissues. Numerous methods are reviewed by Favreau, P, et al, *Toxicon,* 2006; 47: 676-687. MS techniques are readily adaptable to sequencing proteins from crude samples. Shevchenko, A, et al., *Methods Mol. Biol.,* 2000; 146:1-16. Recently, Banderia et al report rapid sequencing of whole proteome from a crude preparation of snake venom. Banderia, N, et al, *Mol. Cell. Proteomics,* 2007; 6:1123-34. These investigators also report use of spectral networks for protein identification. Bandeira, N, et al, *Proc. Natl. Acad. Sci. USA,* 2007; 104:6140-45. These and other methods are suitable for use in the present invention should sequencing of a particular known protein, or unknown protein be desirable.

Target peptide selection is optionally performed for any strain as exemplified by the following process for the complete HA of H5N1 strain A/Vietnam/1203/2004. Tools are well known and available in the art for determining cleavage sites by endoproteases given a recognized primary sequence. For predicting trypsin cleavage sites the ExPASy Peptide Cutter (available at http://www.expasy.ch/tools/peptidecutter/) may be used for an in silico digestion of HA or any target protein. It is appreciated that this may be similarly done by hand or other tools known in the art. Trypsin cleaves proteins C-terminal to lysine and arginine. Thus, Peptide Cutter demonstrates 61 cleavage sites in the illustrative HA. The resulting peptides are listed in Table 2.

TABLE 2

Peptides Resulting from Cleavage of HA from H5N1 strain A/Vietnam/1203/2004.

| Cleavage Site | Peptide Sequence | Peptide Mass (Da) |
|---|---|---|
| 3 | MEK | 406.497 |
| 15 | IVLLFAIVSLVK (SEQ ID NO 7) | 1314.718 |
| 38 | SDQICIGYHANNSTEQVDTIMEK (SEQ ID NO 8) | 2596.823 |
| 51 | NVTVTHAQDILEK (SEQ ID NO 9) | 1467.642 |
| 52 | K | 146.189 |
| 56 | HNGK (SEQ ID NO 10) | 454.486 |
| 69 | LCDLDGVKPLILR (SEQ ID NO 11) | 1454.791 |
| 98 | DCSVAGWLLGNPMCDEFINVPEWSYIVEK (SEQ ID NO 12) | 3315.778 |
| 118 | ANPVNDLCYPGDFNDYEELK (SEQ ID NO 13) | 2316.48 |
| 123 | HLLSR (SEQ ID NO 14) | 624.741 |
| 129 | INHFEK (SEQ ID NO 15) | 786.886 |

TABLE 2-continued

Peptides Resulting from Cleavage of HA from H5N1 strain A/Vietnam/1203/2004.

| Cleavage Site | Peptide Sequence | Peptide Mass (Da) |
|---|---|---|
| 135 | IQIIPK (SEQ ID NO 16) | 710.915 |
| 156 | SSWSSHEASLGVSSACPYQGK (SEQ ID NO 17) | 2168.322 |
| 161 | SSFFR (SEQ ID NO 18) | 642.712 |
| 168 | NVVWLIK (SEQ ID NO 19) | 871.09 |
| 169 | K | 146.189 |
| 177 | NSTYPTIK (SEQ ID NO 20) | 923.034 |
| 178 | R | 174.203 |
| 205 | SYNNTNQEDLLVLWGIHHPNDAAEQTK (SEQ ID NO 21) | 3108.33 |
| 224 | LYQNPTTYISVGTSTLNQR (SEQ ID NO 22) | 2156.38 |
| 228 | LVPR (SEQ ID NO 23) | 483.611 |
| 232 | IATR (SEQ ID NO 24) | 459.546 |
| 234 | SK | 233.268 |
| 241 | VNGQSGR (SEQ ID NO 25) | 716.752 |
| 271 | MEFFWTILKPNDAINFESNGNFIAPEYAYK (SEQ ID NO 26) | 3571.021 |
| 274 | IVK | 358.481 |
| 275 | K | 146.189 |
| 282 | GDSTIMK (SEQ ID NO 27) | 750.865 |
| 293 | SELEYGNCNTK (SEQ ID NO 28) | 1257.337 |
| 320 | CQTPMGAINSSMPFHNIHPLTIGECPK (SEQ ID NO 29) | 2924.418 |
| 323 | YVK | 408.498 |
| 326 | SNR | 375.385 |
| 334 | LVLATGLR (SEQ ID NO 30) | 842.049 |
| 339 | NSPQR | 600.632 |
| 341 | ER | 303.318 |
| 343 | RR | 330.39 |
| 344 | K | 146.189 |
| 345 | K | 146.189 |
| 346 | R | 174.203 |
| 384 | GLFGAIAGFIEGGWQGMVDGWYGYHHSNEQGSGYAADK (SEQ ID NO 31) | 4034.347 |
| 389 | ESTQK (SEQ ID NO 32) | 591.619 |
| 397 | AIDGVTNK (SEQ ID NO 33) | 816.91 |
| 404 | VNSIIDK (SEQ ID NO 34) | 787.911 |
| 414 | MNTQFEAVGR (SEQ ID NO 35) | 1152.29 |
| 421 | EFNNLER (SEQ ID NO 36) | 920.977 |
| 422 | R | 174.203 |
| 428 | IENLNK (SEQ ID NO 37) | 729.831 |
| 429 | K | 146.189 |

TABLE 2-continued

Peptides Resulting from Cleavage of HA from H5N1 strain A/Vietnam/1203/2004.

| Cleavage Site | Peptide Sequence | Peptide Mass (Da) |
|---|---|---|
| 452 | MEDGFLDVWTYNAELLVLMENER (SEQ ID NO 38) | 2788.139 |
| 462 | TLDFHDSNVK (SEQ ID NO 39) | 1175.263 |
| 467 | NLYDK (SEQ ID NO 40) | 651.717 |
| 469 | VR | 273.335 |
| 473 | LQLR (SEQ ID NO 41) | 528.652 |
| 477 | DNAK (SEQ ID NO 42) | 446.461 |
| 489 | ELGNGCFEFYHK (SEQ ID NO 43) | 1443.596 |
| 499 | CDNECMESVR (SEQ ID NO 44) | 1185.307 |
| 513 | NGTYDYPQYSEEAR (SEQ ID NO 45) | 1692.716 |
| 515 | LK | 259.349 |
| 516 | R | 174.203 |
| 523 | EEISGVK (SEQ ID NO 3) | 760.842 |
| 565 | LESIGIYQILSIYSTVASSLALAIMVAGLSLWMCSNGSLQCR (SEQ ID NO 46) | 4464.291 |
| 568 | ICI | 347.473 |

Selection of suitable target peptides based on the above criteria is straightforward and will be appreciated by one having ordinary skill. For the HA example, peptides with 5 residues or fewer are optionally eliminated to increase the probability of recognizing conserved sequences leaving of the original 61 peptides, only 35. It is also appreciated that target peptides with fewer than 15 residues are preferred to simplify synthetic target peptide and standard peptides. Further selecting for the absence of methionine or tryptophan leaves 16 peptides as observed in Table 3.

TABLE 3

Exemplary selected peptides from H5N1 strain A/Vietnam/1203/2004.

| Cleavage Site | Peptide Sequence | Peptide Mass (Da) |
|---|---|---|
| 15 | IVLLFAIVSLVK (SEQ ID NO 47) | 1314.718 |
| 51 | NVTVTHAQDILEK (SEQ ID NO 48) | 1467.642 |
| 69 | LCDLDGVKPLILR (SEQ ID NO 49) | 1454.791 |
| 129 | INHFEK (SEQ ID NO 50) | 786.886 |
| 135 | IQIIPK (SEQ ID NO 51) | 710.915 |
| 161 | SSFFR (SEQ ID NO 52) | 642.712 |
| 168 | NVVWLIK (SEQ ID NO 53) | 871.09 |
| 241 | VNGQSGR (SEQ ID NO 54) | 716.752 |
| 334 | LVLATGLR (SEQ ID NO 55) | 842.049 |
| 339 | NSPQR (SEQ ID NO 56) | 600.632 |
| 389 | ESTQK (SEQ ID NO 57) | 591.619 |

TABLE 3-continued

Exemplary selected peptides from H5N1 strain A/Vietnam/1203/2004.

| Cleavage Site | Peptide Sequence | Peptide Mass (Da) |
|---|---|---|
| 397 | AIDGVTNK (SEQ ID NO 58) | 816.91 |
| 404 | VNSIIDK (SEQ ID NO 59) | 787.911 |
| 421 | EFNNLER (SEQ ID NO 60) | 920.977 |
| 428 | IENLNK (SEQ ID NO 61) | 729.831 |
| 462 | TLDFHDSNVK (SEQ ID NO 62) | 1175.263 |
| 523 | EEISGVK (SEQ ID NO 3) | 760.842 |

A simple BLAST analysis illustratively employing tools available from the National Center for Biotechnology Information allows recognition of conserved sequences. It is recognized in the art that the C-terminus of the HA of the H5N1 strain is highly conserved, and selection of a peptide from this region is most likely to result in sequence conservation for H5 strains. The selected target peptide EEISGVK (SEQ ID NO. 3) resulting from trypsin cleavage at residue 523 demonstrates sequence identity in 91% of the deposited strains. Thus, thus this data combined with the ready recognition in test analysis runs identified this peptide as a suitable target peptide. It is appreciated that other HA peptides are similarly suitable.

In a further non-limiting example an art appreciated similar method is optionally used to identify target peptides in pertussis toxin (PT) which is an immunogenic and toxic component of *Bordetella Pertussis*. PT is an AB endotoxin consisting of 5 subunits of which the S1 subunit serves the active toxic function. Tamura M, et al., *Biochemistry*, 1982; 21:5516-5522; Sekura R D, et al, *J Biol. Chem.*, 1983; 258: 14647-14651. The sequence of PT S1 subunit is known. Cleavage by trypsin produces 25 total cleavage sites. Selection based on preferred length and absence of methionine and tryptophan results in two remaining peptides; IPPENIR (SEQ ID NO 5) and SVASIVGTLVR (SEQ ID NO 6). Either peptide is suitable in the present process. The generation of standard peptides to SVASIVGTLVR (SEQ ID NO 6) is optionally performed by incorporation of mass labeled valine, leucine or other amino acid residue during synthesis.

TABLE 4

Selected peptides from PT cleavage with trypsin.

| Cleavage Site | Peptide Sequence | Peptide Mass (Da) |
|---|---|---|
| 176 | IPPENIR (SEQ ID NO 5) | 837.974 |
| 227 | SVASIVGTLVR (SEQ ID NO 6) | 1101.312 |

Synthesis of standard peptides that are unmodified, mass labeled, or otherwise altered is optionally performed by techniques known in the art. Custom peptide synthesis is available from Sigma-Genosys (The Woodlands, Tex.) or other vendors readily ascertainable in the art. Any synthesis chemistry yielding relatively pure and quantifiable synthetic peptide is suitable for use in the present invention.

The LCMS assay optionally uses LC-isotope dilution mass spectrometry. Alternatively, the LCMS assay uses ultra performance liquid chromatography isotope dilution tandem mass spectrometry (UPLC-ID/MS/MS). UPLC-ID/MS/MS combines both high sample throughput and rapid analysis time with accurate sample analysis and quantitation. Kirkpatrick, et al, *Methods*, 2005; 35:265-273; Mayya, V, et al, *Mol. Cell. Proteomics*, 2006; 5:1146-1157; Brönstrup, M., *Expert Rev. Proteomics*, 2004; 1:503-512; Gerber, S A, et al, *Proc. Natl. Acad. Sci.*, 2003; 100: 6940-6945. This method allows for rapid sample analysis of limited protein or peptide quantity by permitting operational pressures as high as 15,000 psi, particle sizes as low as 1.7 μm, short column lengths, and flow rates as high as 2 ml/min. Nováková, L, et al, *Talanta*, 2006; 68:908-918. In a preferred embodiment, UPLC-ID/MS/MS is coupled with multiple reaction monitoring (MRM) analysis.

An inventive process of quantifying a microorganism protein includes obtaining a microorganism sample, subjecting said sample to digestion, measuring the amount of at least one target peptide produced by said digestion by a liquid chromatography mass spectrometry assay, and quantifying the microorganism protein within the microorganism sample by comparing the amount of the target peptide to a known amount of standard peptide.

The present invention is further illustrated with respect to the following non-limiting examples.

Example 1

Preparation of viral samples: The H1N1 and H5N1 samples are obtained and the H3N2 and B strains are obtained from a commercial preparation of vaccine. The virus components are purified via cesium chloride (CsCl) equilibrium density gradient centrifugation. A discontinuous step gradient of 26%, 32%, 45% and 63% CsCl was under laid into 5 mL thin walled polyallomar ultracentrifugation tubes containing 1 mL sample as described in Sambrook, J. et al, *Molecular Cloning: A Laboratory Manual,* 2ed.; Cold Spring Harbor Laboratory Press, 1989, and centrifuged in a Sorvall Discovery M150 SE Micro-Ultracentrifuge (Thermo Scientific, Milford, Mass.) equipped with a swinging bucket rotor (S520ST) for 24 hours (40,000 rpm, 4° C.). 0.5 mL fractions are collected from the tubes using a sterile 20 gauge needle to puncture the tube. Each fraction is washed twice with 50 mM ammonium bicarbonate through a 10 kDa regenerated nitrocellulose molecular weight cutoff filter (Millipore, Billerica, Mass.) and resuspended in 50 μL (final) of 50 mM ammonium bicarbonate.

Choice of target peptides: Selection of target peptides is based on signal intensity, prevalence of full protease digestion, absence of split charge states, and absence of methionine and tryptophan. Peptides are evaluated for degree of conservation based on influenza subtype as obtained from the NCBI Influenza Virus Resource and aligned using Muscle 3.6. Peptides chosen for analysis of strains H1, H3, H5, and HB are listed in Table 5.

TABLE 5

| subtype | Target peptide | Total # strains in database | # of strains with sequence at this position | # of strains with identical sequence as target peptide | % |
|---|---|---|---|---|---|
| H1 | EQLSSVSSFER (SEQ ID NO 1) | 1183 | 1156 | 1019 | 88 |
| H3 | STQAAINQINGK (SEQ ID NO 2) | 3676 | 1739 | 1204 | 69 |
| H5 | EEISGVK (SEQ ID NO 3) | 1542 | 1040 | 951 | 91 |
| HB | NLNSLSELEVK (SEQ ID NO 4) | 1459 | 194 | 191 | 98 |

In particular, the peptide chosen form the HB subtype (NLNSLSELEVK SEQ ID NO. 4) is present near the C-terminus of the HB protein. Although there was not 100% sequence information in this region for all 1459 strains, the known 194 strains showed 97% identity in this region. Further, should additional strains be sequenced and a polymorphism or other mutation is observed in this region, it is well within the skill of the art to synthesize standard peptides to the sequence without undue experimentation. Peptides from SEQ ID NOs 1-4 are chosen for further characterization, however, it is appreciated that other peptides are similarly suitable.

Example 3

Peptide target determination via LC/MS/MS: Prior to digestion to solubilize hemagglutinin target proteins, 90 μL of a 0.1% solution of the acid liable detergent Rapigest (Waters, Bedford, Mass.) is added to 10 μL of the viral protein solution. The protein concentration is measured and it is estimated that 2-10 μg of hemagglutinin was digested in each sample. Proteins are incubated overnight at 37° C. with 100 pmol of modified trypsin (Promega, Madison, Wis.) for complete protein digestion. The protein digest (5 μl) was injected onto a Symmetry300™ (Waters, Bedford, Mass.) $C_{18}$ column with dimensions of 150 mm×0.320 mm i.d. Mobile phase A was 0.1% formic acid (Fluka Biochemica, Switzerland) in water (Sigma Aldrich, St. Louis, Mo.) while mobile phase B is 0.1% formic acid in acetonitrile (Burdick & Jackson, Muskegon, Mich.). Chromatography is completed with a Waters Nano-Acquity at a flow rate of 3 μL/min and a gradient beginning at 5% B and continuing to 50% B in 60 minutes. MS/MS experiments are performed on a Waters QTOF Premier. The PepSeq program within Water's BioLynx software package is used for de novo analysis of the sequence (MS/MS) data. MS-Pattern of Protein Prospector used the sequence tag determined from PepSeq to search the nonredundant database of the National Center for Biotechnology Information (NCBI) for protein identification. Peptides are selected based on their respective signal intensities, lack of missed cleavage sites, absence of split charge states, and the absence of methionine and tryptophan in the peptide sequence. The entire family of peptides for each hemagglutinin is analyzed. The peptides selected (SEQ ID NOs 1-4) are listed along with the inter-strain sequence conservation in Table 1.

Synthesis of Labeled Internal Standards:

Peptides are synthesized by Sigma Genosys (The Woodlands, Tex.) and are provided in Table 3. For H1N1 strains, a labeled analog of the target peptide is made by incorporating phenylalanine with 13C and 15N to give a peptide that is 10 Da heavier than the native peptide. For H3N2 and B strains, an isoleucine and leucine respectively are 13C and 15N labeled resulting in peptides, in each case, that are 7 Da heavier than the native peptide. The valine of H5N1 is labeled with 13C and 15N to give a labeled peptide that is 6 Da Hans higher than the native peptide. These are packaged in 1 nmol/vial quantities by the manufacturer. In addition to the manufacturer's initial amino acid analysis (AAA) necessary for proper vial aliquoting, AAA of the peptide content is independently analyzed at the W.M. Keck Foundation Biotechnology Resource Laboratory at Yale University (New Haven, Conn.) and by Commonwealth Biotechnologies (Richmond, Va.).

Example 4

Synthesis of Standard Peptides: Peptide sequences are chosen based on the sequence of target peptides determined in prior experiments as optimized for quantification. Standard peptides are synthesized by Sigma Genosys (The Woodlands, Tex.) and are provided in Table 5 (target peptide). The labeled residue is bold and underlined in target SEQ ID NOs 1-4 as SEQ ID Nos 63-66. (Table 6).

TABLE 6

| target peptide | Influenza subtype | observed m/z | ms/ms ion (quantitation) | ms/ms ion (confirmation) | ms/ms ion (confirmation) |
|---|---|---|---|---|---|
| EQLSSVSSFER (SEQ ID NO 1) | H1 | 634.8 (+2) | 1011.6 (y9) | 625.2 (y5) | 898.4 (y8) |
| EQLSSVSSFER (SEQ ID NO 63) | H1 | 639.8 (+2) | 1021.6 (y9) | — | — |
| STQAAINQINGK (SEQ ID NO 2) | H3 | 622.8 (+2) | 857.5 (y8) | 786.4 (y7) | 928.5 (y9) |
| STQAAINQINGK (SEQ ID NO 64) | H3 | 626.3 (+2) | 864.6 (y8) | — | — |
| EEISGVK (SEQ ID NO 3) | H5 | 761.4 (+1) | 503.4 | 390.2 (y4) | 303.2 (y3) |
| EEISGVK (SEQ ID NO 65) | H5 | 767.4 (+1) | 509.4 | — | — |
| NLNSLSELEVK (SEQ ID NO 4) | HB | 623.3 (+2) | 704.4 (y6) | 904.4 (y8) | 1018.4 (y9 |
| NLNSLSELEVK (SEQ ID NO 66) | HB | 626.8 (+2) | 711.4 (y6) | — | — |

For H1N1 strains, a labeled analog of the target peptide is made by incorporating phenylalanine with $^{13}$C and $^{15}$N to generate a peptide that is about 10 Da heavier than the native peptide. For H3N2 and B strains, an isoleucine and leucine respectively are $^{13}$C and $^{15}$N labeled resulting in peptides, in each case, that are about 7 Da heavier than the respective native peptide. The valine of H5N1 is labeled with $^{13}$C and $^{15}$N to give a labeled peptide that is about 6 Da higher than the native peptide. Synthesized standard peptides are packaged in 1 nmol/vial quantities by the manufacturer. In addition to the manufacturer's initial amino acid analysis (AAA) necessary for proper vial aliquoting, AAA of the peptide content is independently analyzed at the W.M. Keck Foundation Biotechnology Resource Laboratory at Yale University (New Haven, Conn.) and by Commonwealth Biotechnologies (Richmond, Va.).

Preparation of Stocks, Working Stocks and Calibration Solutions

Figure 2:
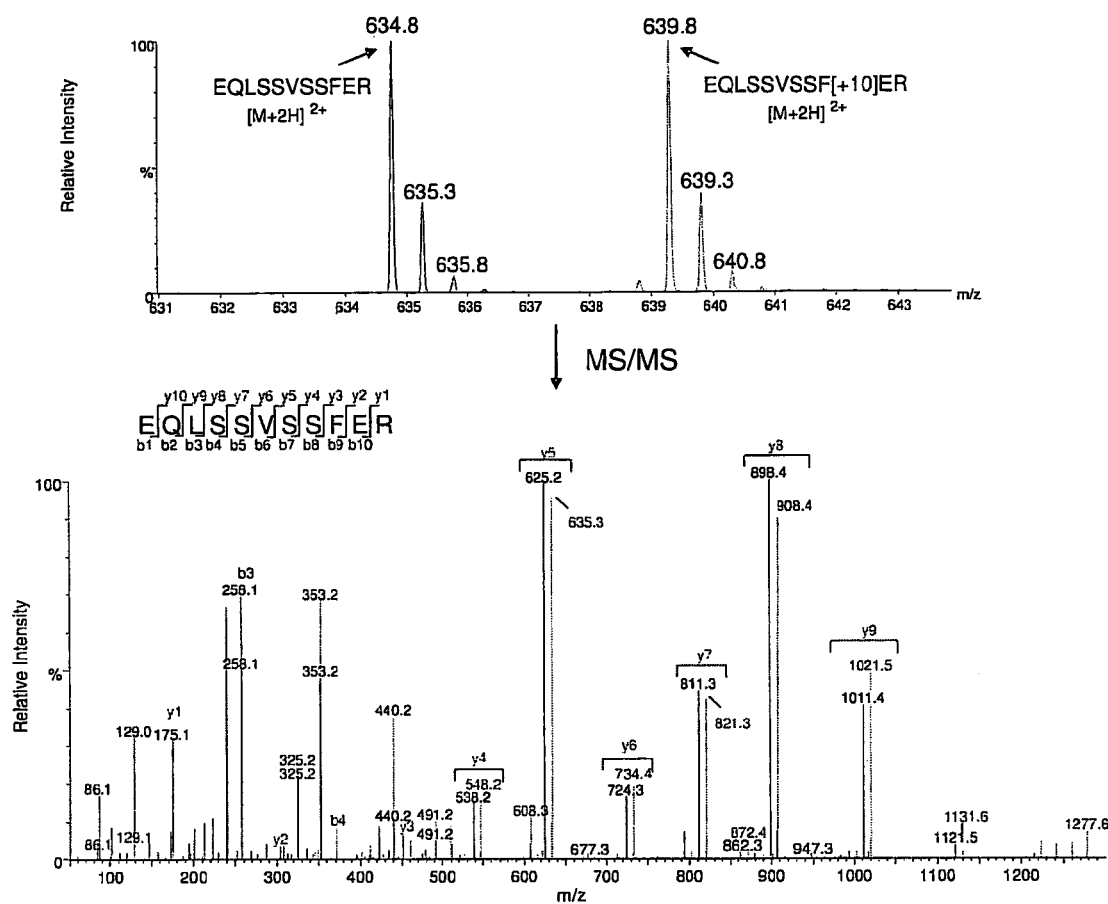
FIG. 2 represents the MS and MS/MS spectra of an exemplary peptide from H1 and its isotopically-enriched counterpart.

Five pmol/μL stock solutions are prepared from purified lyophilized synthetic peptides—one native and one that had been isotopically labeled (Sigma, St. Louis, Mo.) at one amino acid in each sequence for each species to be quantified. The hemagglutinin species HA3, HA1, and HB native and labeled peptides are each reconstituted in 20 μL of 10% formic acid and 180 μL of 0.1% formic acid as per manufacturer instructions. Working stock solutions of each native and labeled peptide internal standard (ISTD) are prepared at a concentration of 0.5 pmol/μL by taking 40 μL of the stock solution and diluting into 360 μL of 0.1% formic acid. Each ISTD is isotopically labeled with 13C and or 15N to provide mass differences of +7 or +10 Da (FIG. 1). Five 500 μL calibration standards: 10, 30, 50, 70, and 90 fmol/μL respectively, is prepared from the working stock solutions. For each calibration standard the labeled peptide is 50 fmol/μL.

The concentrations of the peptide standards in the five standards used for calibration. The concentration of the labeled peptide spiked into the standards is constant in all five calibration points.

| Calibration Standard | H1 unlabeled (fmol/μL) | H1 labeled (fmol/μL) | H3 unlabeled (fmol/μL) | H3 labeled (fmol/μL) | HB unlabeled (fmol/μL) | HB labeled (fmol/μL) |
|---|---|---|---|---|---|---|
| 1 | 10 | 50 | 10 | 50 | 10 | 50 |
| 2 | 30 | 50 | 30 | 50 | 30 | 50 |
| 3 | 50 | 50 | 50 | 50 | 50 | 50 |
| 4 | 70 | 50 | 70 | 50 | 70 | 50 |
| 5 | 90 | 50 | 90 | 50 | 90 | 50 |

Three replicate injections are performed for each calibration standard solution containing all three synthetic peptide analogues ranging in concentration from 10-90 fmol/μL with corresponding labeled peptides spiked at 50 fmol/μL. The mean area ratios (unlabeled/labeled) are plotted against expected concentrations for each standard. Linear regression without weighting is applied to the data sets and calibration curves generated for each peptide. Regression analysis resulted in equations of $y=68.958x-0.5992$, $y=29.972x+2.4036$, and $y=41.146x+1.3843$ with corresponding $R^2$ values of 0.9965, 0.9975, and 0.9940 for H3, H1, and HB respectively.

Example 5

Preparation of Working Stocks: all Synthesized Peptides are Reconstituted as Per the manufacturer's instructions. Each vial contained 1 nmol of peptide to which 20 μL of 10% (v/v) aqueous formic acid solution is added, and the sample is vortexed to fully dissolve the peptide. A 5 pmol/μL stock solution is prepared by addition of 180 μL of 0.1% formic acid. Five 0.5 mL stock calibration standards ranging from 10-90 fmol/μL are prepared by adding 10, 30, 50, 70, and 90 μL of each of the unlabeled peptides, 50 μL of each of the labeled peptides, and 0.1% formic acid to make the final volume 0.5 mL. The final concentrations of each calibration standard for the different strains are provided in Table 5. The 0.5 μmol/μL spike solutions of the labeled peptides are used for the internal standards (ISTD).

Example 6

Preparation of vaccine target peptides for analysis: Unlike prior art procedures, no sample cleanup is required prior to preparation of samples for analysis, thus preserving and optimizing quantification by eliminating commonly unpredictable recovery steps from the cleanup procedure. Five μL of vaccine from 550 (±10) μL vials are diluted in 10 μL of Rapigest (Waters Corporation, Milford, Mass.). The samples are heated for five minutes at 100° C. After cooling to room temperature, 5 μL (~100 μmol) of sequencing grade modified trypsin (Promega, Madison, Wis.) is added to each sample and incubated at 37° C. for 2 hours. Digests are allowed to cool and 50 μL of water is added along with 10 μL of each of the 0.5 pmol/μL H3, H1, and HB labeled ISTD working stock solutions. The digested samples are mixed, centrifuged for 10 seconds (3,000×g), and transferred to autosampler vials for analysis.

FIG. 1 demonstrates a complex total ion chromatogram. However, extracted ion chromatograms are easily obtained from this complex mixture by application of the instant inventive process. To be certain that the extracted ions are indeed the target peptide, the samples are further analyzed by a second stage mass spectrometry fragmentation analysis. (MS/MS). In the selected influenza strains similar mass peaks are isolated with retention times longer than 25 minutes, hence different than the target peptides. The charge on these peptides is single, whereas the target peptides are doubly charged due to detergent present in the samples. Target peptide sequences are confirmed by MS/MS. For example, FIG. 2 demonstrates the extracted ion chromatogram of H1 target peptide SEQ ID NO. 1 and its corresponding (10+) mass labeled standard peptide SEQ ID NO. 63. MS/MS analysis confirmed the sequence of the target peptide through the b-ion and the y-ion fragmentation series. A 10 Da shift is observed in all fragmentation ions $y_3$ to $y_{10}$ relative to its unlabeled counterpart. (FIG. 2) Thus, both the unlabeled target peptide and unlabeled standard peptide are simultaneously observable at similar signal intensities.

The labeled standard peptides have identical LC retention and mass spectrometry characteristics although they possess unique total mass parameters. Thus, although vaccine digests contain detergents and other additives the instant inventive process provides an unexpectedly high degree of selectivity in complex matrices by simultaneously monitoring an intact peptide's mass, charge state, and one or more of its fragment ions along with the same parameters of the isotopically labeled standard peptide.

Example 7

The method is also demonstrated for the quantitative analysis of H5. The amino acid sequence of the H5N1 strain A/Vietnam/1203/2004 strain provided the following target peptide used for this example EEISGVK (SEQ ID NO 3). FIG. 6 shows a typical MRM chromatogram of the native and the labeled H5 peptides that are obtained from Sigma Genosys and used to generate a calibration curve with a linear regression equation of y=49.697+5.227 and an $R^2$=0.991. Since an H5 vaccine is not available for analysis, the method is demonstrated on a purified A/Vietnam/1203/2004 virus strain (data not shown). The same procedure is followed as for the seasonal vaccine. Four digest preparations of the purified virus are run in quadruplicate and are determined to contain 33.44±0.60 fmol/μL of H5 hemagglutinin.

Example 8

Quantifying target peptide and sample protein by LC/MS/MS: The binary solvent and sample managers on the Nano- Acquity system (Waters Corporation, Milford Mass.) are configured for capillary flow rates using 0.001" Peeksil tubing from the injector on the sample manager to the head of the analytical column. The analytical column utilized is a 150 mm×1 mm i.d. Symmetry300 reverse phase $C_{18}$ (3.5 µm particle size, Waters Corporation, Milford, Mass.). The aqueous mobile phase (A) consisted of HPLC grade water with 0.1% formic acid, while the organic phase (B) is acetonitrile (ACN) with 0.1% formic acid. A 2 µL full loop injection with 3 time loop overfill is utilized for injections. The needle draw rate is set to 5 µL/min. Both pre and post injection, the injection needle is washed with 200 µL of mobile phase B followed by a 600 µL of weak wash solution of 95% HPLC grade water, 5% ACN, and 0.1% formic acid. A gradient profile is utilized at a flow rate of 30 µL/min. Initially, the mobile phase consisted of 95% A and 5% B. At minute 10 the gradient is stepped to 12% B. A 1.1% change per minute is utilized over the next 14 minutes where the mobile phases are 73% A and 27% B respectively. At minute 24 the gradient is stepped to 5% A and 95% B for 20 minutes to clean the column, then stepped to 95% A and 5% B for the next 30 minutes to equilibrate column to initial conditions. The total run time is 74 minutes. Initial injection volume is 24

The column eluent is introduced into a Thermo Quantum TSQ triple quadrupole tandem mass spectrometer with an electrospray interface (Thermo Scientific, Waltham, Mass.). The instrument is operated in the positive ion mode with multiple reaction monitoring (MRM), m/z quantifying transitions pairs of: 622.8/857.5, 634.8/1011.4, and 623.3/704.4 for the H3, H1, and HB native peptides and 626.6/864.5, 639.8/1021.4, and 626.8/711.4 for the corresponding labeled peptides. For H5, the native pair of 761.4/503.4 and the labeled pair of 767.4/509.4 are monitored. Thus, each transition is comprised of a monoisotopic ion precursor and a selected monoisotopic product ion. It is appreciated that other product ions are similarly suitable. Two additional transition pairs utilizing the same conditions are monitored for peptide conformation and are provided in Table 6. Instrument parameters are as follows: spray voltage 4000 V, sheath gas 4, auxiliary gas 2, capillary tube temperature 300° C., and a collision gas of 1.5 mTorr. Collision energies and tube lens are optimized for each peptide pair transition and corresponding ISTD. Data processing and instrument control are performed with the Thermo Scientific Xcalibur software.

Figure 3:
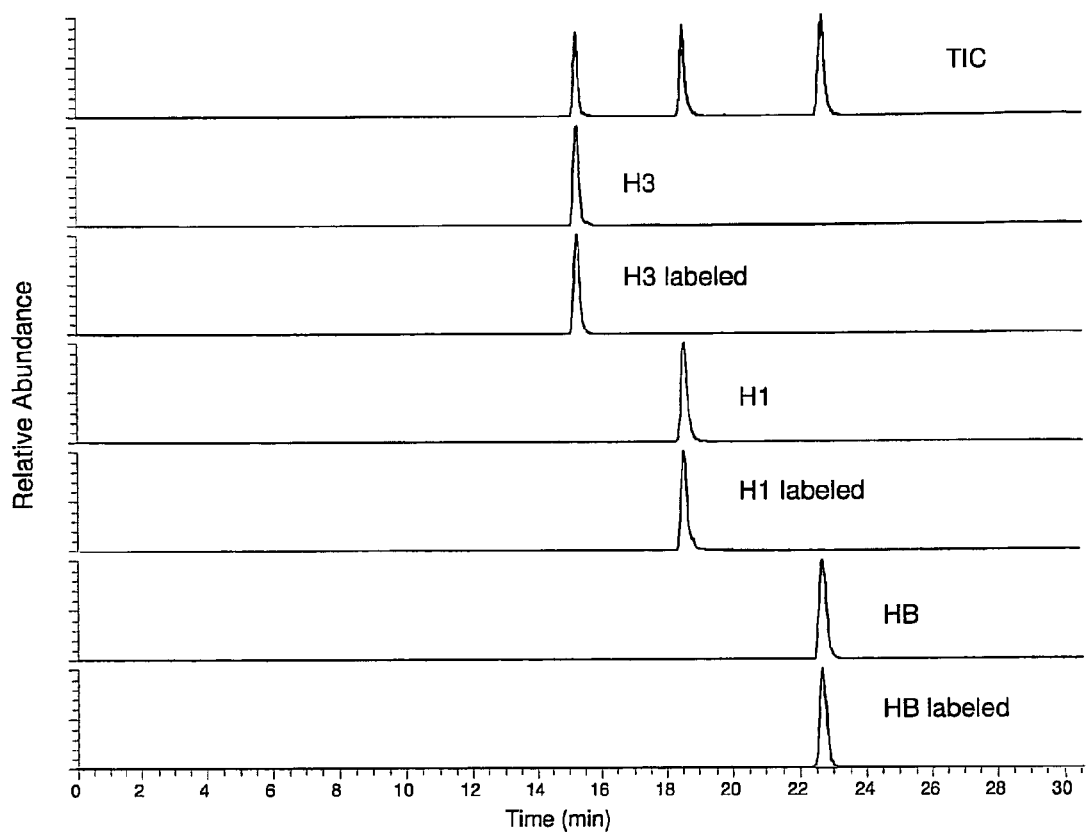
FIG. 3 represents the liquid chromatography MRM chromatograms of three exemplary influenza strains present in a commercial preparation of influenza vaccine illustrating peptides and standard peptides from each strain.
Figure 5:
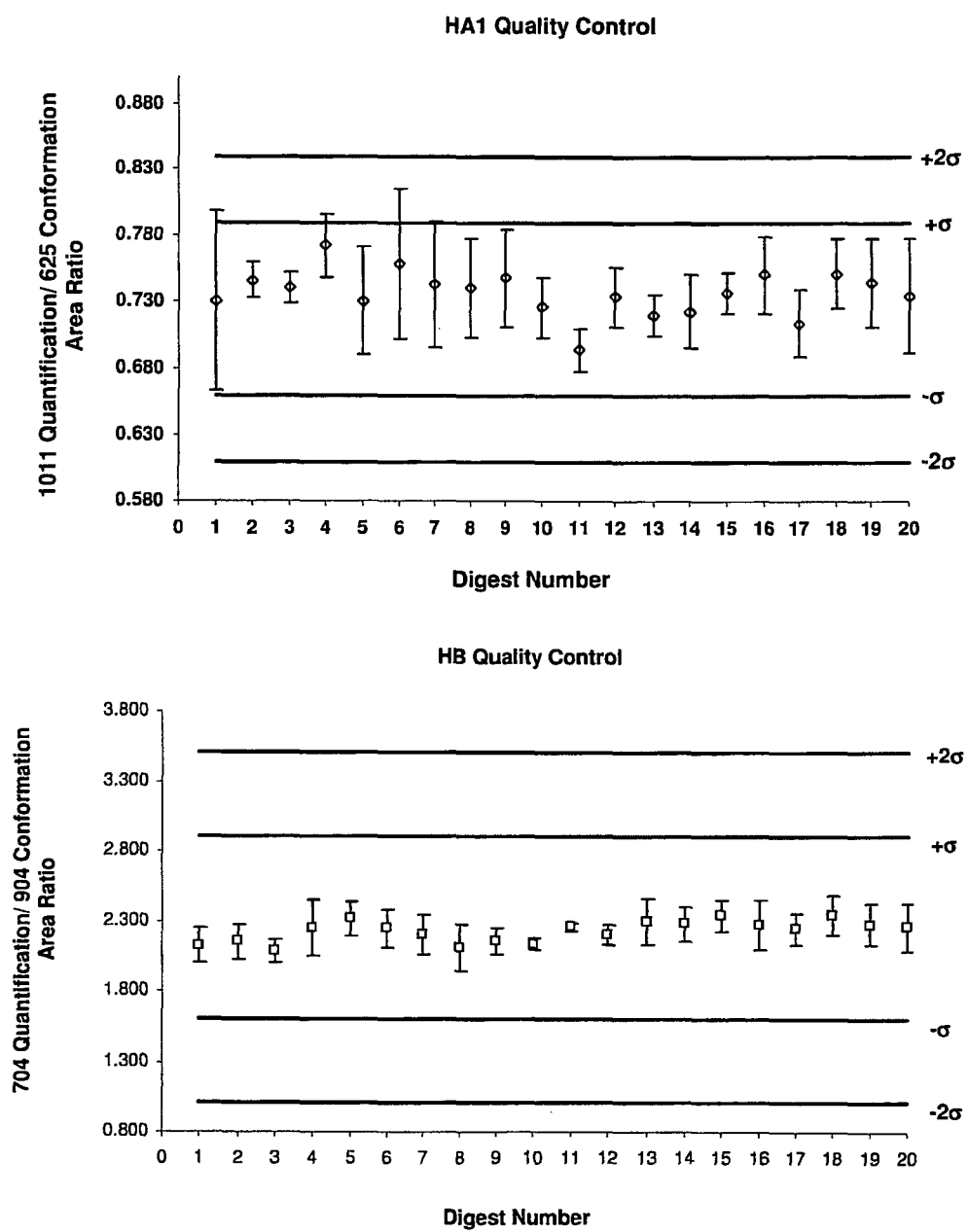
FIG. 5 represents the ratio of the quantitative ion of H1 to the confirmation ion of H1 indicating tolerance limits ($\sigma$)
Figure 6:
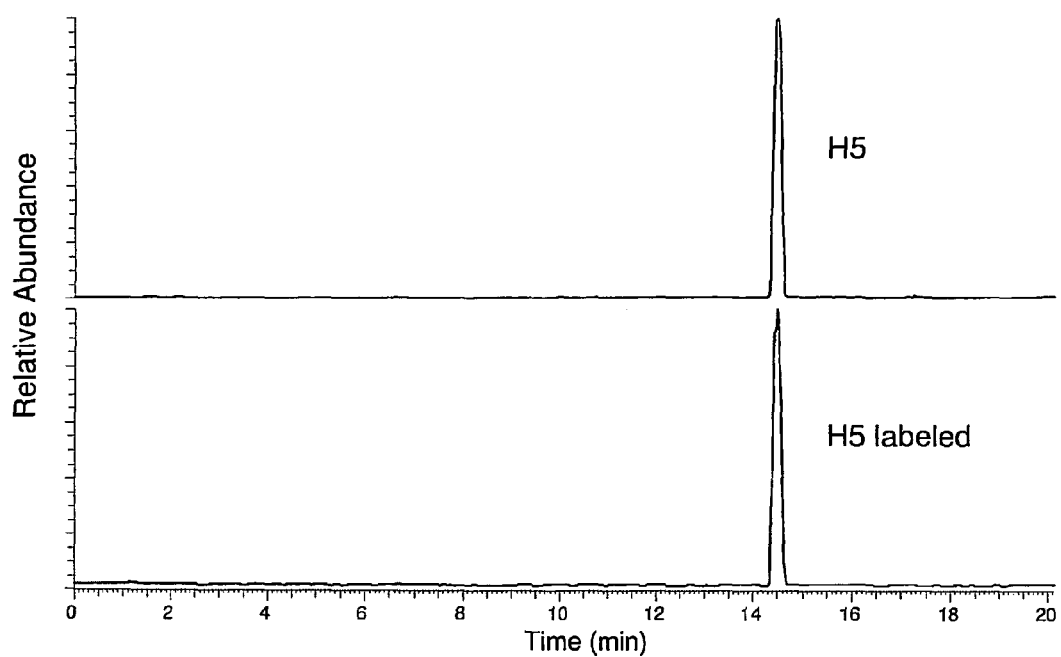
FIG. 6 represents a liquid chromatography multiple reaction monitoring chromatograms of H5.

Precision of the method is determined by preparation and analysis of 20 repeat digest preparations from the same vial of sample vaccine. FIG. 3 illustrates a sample family of MRM chromatograms from a commercially prepared trivalent vaccine preparation. As is readily observed the chromatograms are free from contaminants and demonstrate robust signal/noise demonstrating the unexpectedly high degree of selectivity of the instant inventive process.

Four replicate injections are performed and analyzed. Results are depicted in FIG. 4. The mean, standard deviation, and percent relative standard deviation (% RSD) of the 20 sample preparations are determined from the average of the four replicates. The digest preparations demonstrated 22.03±1.24 fmol/µL of H3, 32.50±1.14 fmol/µL of H1, and 51.77±5.04 fmol/µL of HB with % RSD of all strains under 10%. The % RSD for H1 and H3 is under 6%.

The total amounts of each HA species in the commercial preparation of vaccine is calculated from the above replicate analysis. Taking into account the dilution factor of 20 (5 uL of vaccine in a 100 µL preparation), the average molecular mass of HA, and the volume of a dose (500 µL), the amounts of H3, H1, and HB in each dose of vaccine are calculated to be 15.42±0.87, 22.75±0.80, and 36.24±3.53 µg/dose respectively.

Example 9

Analysis of Trivalent Vaccine by UPLC-ID/MS/MS: The analytical column is a UPLC BEH 50×2.1 mm id reverse phase $C_{18}$ (1.7 µm particle size, Waters Corporation, Milford, Mass.). The aqueous mobile phase (A) consisted of HPLC grade water with 0.1% formic acid. The organic phase (B) is acetonitrile (ACN) with 0.1% formic acid. Sample is injected at a temperature of 4° C. with a 2 µL full loop injection and a 5.6 time loop overfill. The needle draw rate is 10 µL/min. Both pre- and post-injection, the injection needle is washed with 200 µL of mobile phase B followed by a 600 µL of weak wash solution of 98% HPLC grade water, 2% ACN, and 0.1% formic acid. A gradient at a flow rate of 300 µL/min is used. Initially, the mobile phase consisted of 98% A and 2% B and held for 2 minutes. An 8.3% change per minute is utilized over the next 3 minutes where the mobile phases are 73% A and 27% B respectively. At 5.10 minutes the gradient is stepped to 2% A and 98% B for 3.2 minutes to clean the column, then stepped to 98% A and 2% B for the next 4.5 minutes to re-equilibrate column to initial conditions. The total run time is 12.7 minutes. This selected run time included a 2 minute hold using initial conditions so as to equilibrate the peptides loaded onto the column. During the 2 minute hold approximately 3.8 column volumes of solvent are passed through the system prior to initiation of gradient elution.

Figure 7:
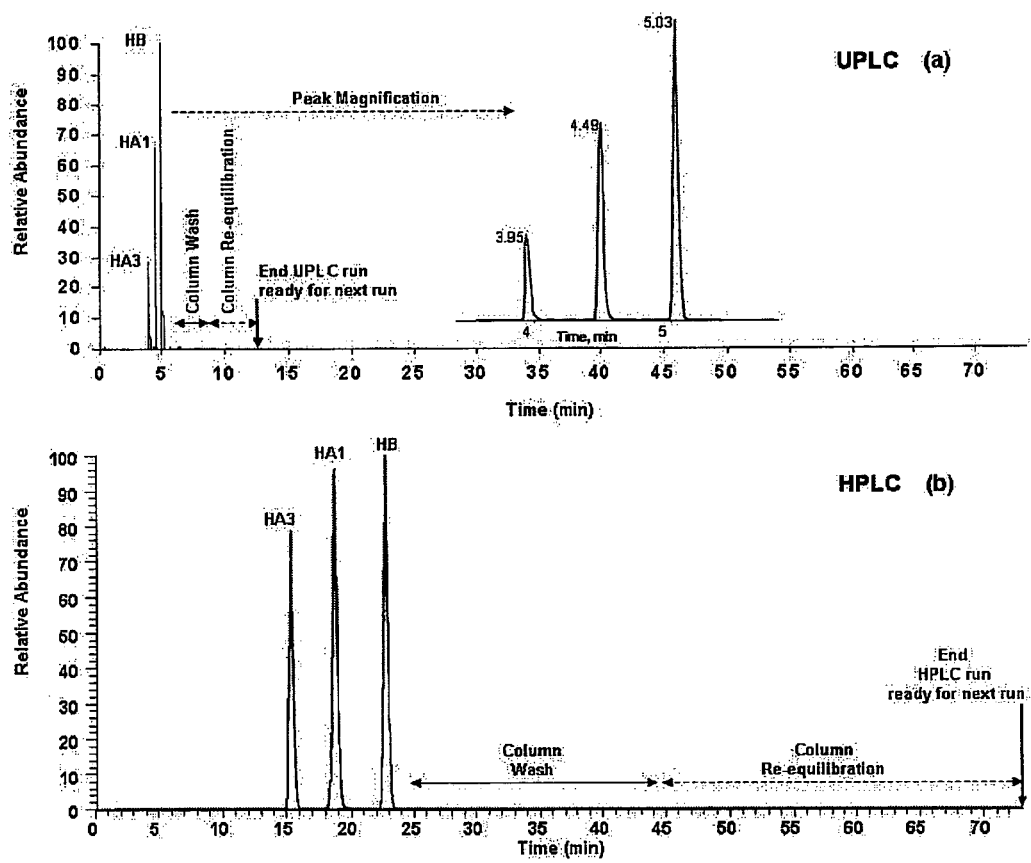
FIG. 7 represents a total ion chromatogram illustrating the reduced analysis times for a UPLC method relative to an HPLC method.

The 3 minute gradient elution to 27% B eluted all peptides in 5.7 column volumes of solvent, while 6.1 and 8.5 column volumes are utilized respectively for column washing and re-equilibration to initial conditions. Under these conditions the column is sufficiently washed so as no inter-run carryover is observed. Highly reproducible peaks are observed with mean retention times of 3.95(±0.010), 4.49 (±0.004), and 5.03(±0.003) minutes for HA3, HA1, and HB unlabeled and labeled peptides respectively. (FIG. 7)

Peak symmetry is excellent with no significant peak fronting and negligible tailing. Asymmetry factor values ranged from 0.8 to 1.4 for all native and labeled peptides. Peak width measured at half peak height ranged from 2.98 to 3.1 seconds for native target peptides and 3.02 to 3.09 for labeled standard peptides. Elution profiles are improved over conventional HPLC techniques as evidenced by half height peak widths of approximately 25% of those observed in prior art assay systems.

Each respective set of quantitation, ISTD, and confirmation ion transition pairs are further divided into periods to provide a total period scan time including pauses of 0.58 seconds. Average base-to-base peak widths of 13.26(±1.89), 17.03 (±0.57), 14.02 (±2.02), 17.26 (±1.51), 17.49 (±0.73), and 17.96(±1.10) seconds are obtained for HA3, HA1, HB unlabeled and labeled peptide standards respectively. Since the dwell time for each ion is 110 msec and the total cycle time per period is 0.52 seconds, a minimum of 23 data points across these narrow peaks is obtained.

Example 10

Figure 9:
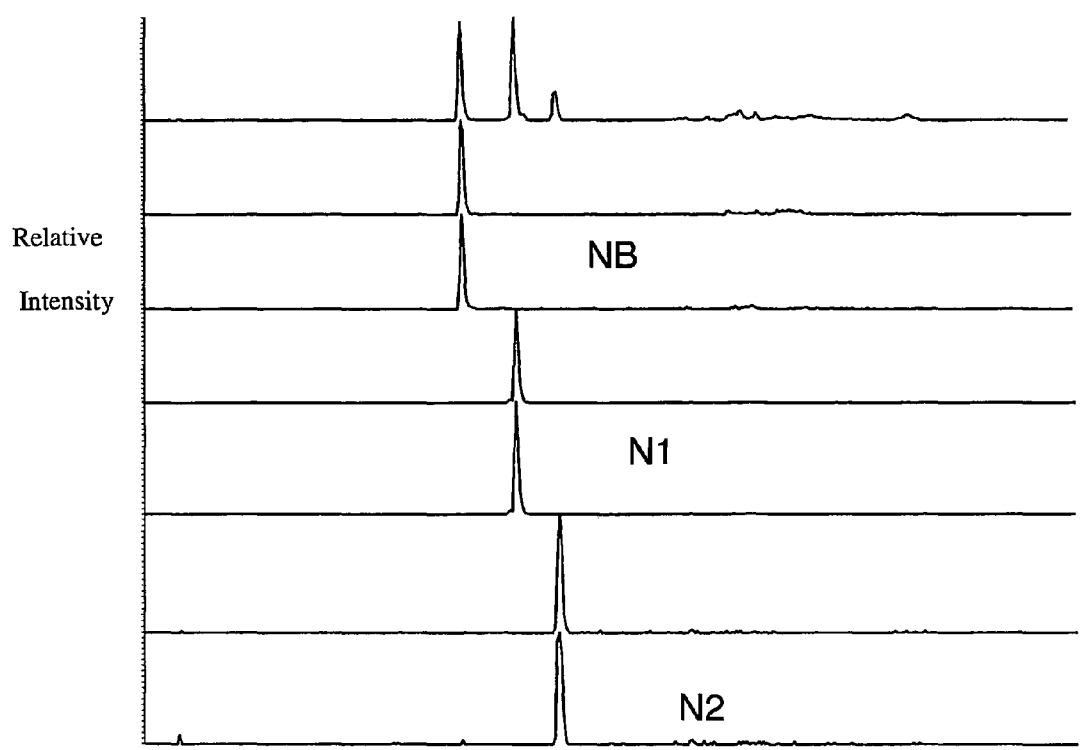

Analysis of UPLC samples by MRM: The column eluent is introduced into an API 4000-Q trap (Applied Biosystems, Foster City, Calif.) triple quadrupole tandem mass spectrometer with a turbo ion spray interface. The instrument is operated in the positive ion mode with segmented multiple reaction monitoring (MRM) monoisotopic mass-to-charge (m/z)

quantifying transitions pairs of: 622.8/857.5, 634.8/1011.4, and 623.3/704.4 for HA3, HA1, and HB native peptides respectively and 626.3/864.5, 639.4/1021.4, and 626.8/711.4 for the corresponding labeled peptides. Two additional transition pairs utilizing the same conditions are monitored for peptide confirmation. A complete list of the transitions is provided in Table 7 along with the optimized declustering potential and collision energies for each peptide transition pair. Instrument parameters are as follows: curtain gas 25, collision gas high, ion spray voltage 5500 V, source temperature of 400° C., source gases 40, cell entrance 5, collision cell exit potential of 13, dwell time of 110 ms per transition. Instrument control and data processing are performed with the Applied Biosystems Analyst software version 2.1.4. The automated baseline-to-baseline peak integration algorithm within the Analyst software is utilized to define peak areas for quantification. In order to determine the precision of the method, 20 tryptic digest preparations were performed from the same vial of a commercial seasonal trivalent vaccine containing H1, H3, and B HAs. A representative series of MRM chromatograms of this experiment are shown in FIG. 9 for NB, N1, and N2. Of the total 100 _L sample preparation, only 2 μL was injected onto the LC column and analyzed by MS/MS. The chromatograms contain no other peaks in the expected retention time windows, confirming the high selectivity of the MRM method. Four replicate injections were averaged for each of 20 samples preparations.

TABLE 7

| Protein | Ion Type/Peptide | Monoisotopic Transition Pairs | | Declustering Potential | Collision Energy |
|---|---|---|---|---|---|
| | | Precursor | Product | | |
| HA3 | Native quantifying STQAAINQINGK (SEQ ID NO 2) | 622.8 | 857.5 ($y_8$) | 70 | 28 |
| HA3 | Labeled ISTD STQAAINQI(+7)NGK (SEQ ID NO. 64) | 626.3 | 864.5 ($y_8$) | 70 | 28 |
| HA3 | Native confirmation STQAAINQINGK (SEQ ID NO 2) | 622.8 | 786.5 ($y_7$) | 70 | 28 |
| HA3 | Native confirmation STQAAINQINGK (SEQ ID NO 2) | 622.8 | 928.5 ($y_9$) | 70 | 28 |
| HA1 | Native quantifying EQLSSVSSFER (SEQ ID NO 1) | 634.8 | 1011.4 ($y_9$) | 76 | 32 |
| HA1 | Labeled ISTD EQLSSVSSF(+10)ER (SEQ ID NO 63) | 639.8 | 1021.4 ($y_9$) | 76 | 32 |
| HA1 | Native confirmation EQLSSVSSFER (SEQ ID NO 1) | 634.8 | 625.2 ($y_5$) | 76 | 32 |
| HA1 | Native confirmation EQLSSVSSFER (SEQ ID NO 1) | 634.8 | 898.4 ($y_8$) | 76 | 32 |
| HB | Native quantifying NLNSLSELEVK (SEQ ID NO 66 | 623.3 | 704.4 ($y_6$) | 76 | 32 |
| HB | Labeled ISTD NLNSLSEL(+7)EVK (SEQ ID NO 4 | 626.8 | 711.4 ($y_6$) | 76 | 32 |
| HB | Native confirmation NLNSLSELEVK (SEQ ID NO 4) | 623.3 | 904.4 ($y_8$) | 76 | 32 |
| HB | Native confirmation NLNSLSELEVK (SEQ ID NO 4) | 623.3 | 1018.4 ($y_9$) | 76 | 32 |

Standard calibrations are performed by quantifying four replicate injections for each solution containing three standard peptides per solution. The concentration ranges for the standard peptides is 10-90 fmol/µl. Calibration curves are generated for each peptide by plotting the mean area ratios (target peptide/standard peptide) against the known concentrations for each standard peptide and analysis by linear regression. The resulting plots are substantially linear with $R^2$ values of 0.9943, 0.9932, and 0.9966 with a corresponding 95% confidence error of ±1.63, ±1.76, and ±1.01 for HA3, HA1, and HB respectively. The lines for HA3, HA1, and HB produced equations of y=58.400x+1.290, y=34.800x+0.2220, and y=31.200x+0.4250, respectively.

Quantifying vaccine samples is performed by four replicate analyses of target peptides generated from one hour trypsin digests. Thus, 20 replicate runs are performed for the three vaccine components HA3, HA1, and HB. Quantitation is performed by computing the area ratio of the target peptide to the standard peptide and applied to the calibration curve producing calculated concentrations for each protein in fmol/µl. Exemplary results are illustrated in Table 8.

TABLE 8

| | | Calculated Protein Concentration | | | | | |
|---|---|---|---|---|---|---|---|
| Digest | Protein Digested µL | HA3 Area Ratio | HA3 fmol/µL | HA1 Area Ratio | HA1 fmol/µL | HB Area Ratio | HB fmol/µL |
| 1 | 10.00 | 0.56 | 33.80 | 1.02 | 35.50 | 2.24 | 70.60 |
| 1 | 10.00 | 0.59 | 35.70 | 1.09 | 37.90 | 2.12 | 66.80 |
| 1 | 10.00 | 0.55 | 33.20 | 1.08 | 37.50 | 2.22 | 70.00 |
| 1 | 10.00 | 0.50 | 30.40 | 1.01 | 35.10 | 2.32 | 73.10 |
| 2 | 10.00 | 0.55 | 33.00 | 1.07 | 37.10 | 2.19 | 69.10 |
| 2 | 10.00 | 0.49 | 29.70 | 1.03 | 35.70 | 2.14 | 67.30 |
| 2 | 10.00 | 0.49 | 29.50 | 1.04 | 36.00 | 2.23 | 70.20 |
| 2 | 10.00 | 0.55 | 33.40 | 1.00 | 34.70 | 2.13 | 67.20 |
| 3 | 10.00 | 0.55 | 33.00 | 1.08 | 37.40 | 2.49 | 78.30 |
| 3 | 10.00 | 0.56 | 33.90 | 1.09 | 38.00 | 2.44 | 76.80 |
| 3 | 10.00 | 0.57 | 34.20 | 1.10 | 38.30 | 2.31 | 72.70 |
| 3 | 10.00 | 0.60 | 35.90 | 1.11 | 38.50 | 2.41 | 75.90 |
| 4 | 10.00 | 0.49 | 29.50 | 1.02 | 35.50 | 2.29 | 72.10 |
| 4 | 10.00 | 0.51 | 30.60 | 1.04 | 36.00 | 2.22 | 69.90 |
| 4 | 10.00 | 0.53 | 31.80 | 1.00 | 34.50 | 2.13 | 67.00 |
| 4 | 10.00 | 0.52 | 31.20 | 1.05 | 36.50 | 2.13 | 66.90 |
| Mean | | | 32.43 | | 36.51 | | 70.87 |
| ±SD | | | 2.10 | | 1.32 | | 3.69 |
| % RSD | | | 6.47 | | 3.60 | | 5.21 |

HA3, HA1, and HB are observed at mean concentration values of 32.43(±2.10), 36.51 (±1.32), and 70.87(±3.69) fmol/µL, with corresponding relative standard deviation values of 6.47%, 3.60% and 5.21% respectively. Three hour digests are also analyzed by similar parameters producing mean protein concentrations within the standard deviations obtained in the one hour digests indicating that complete digestion is achieved in one hour. Finally, calibration standards are run following the experimental procedure and demonstrated no significant alteration in calibration parameters demonstrating the stable nature of the inventive assay system.

The methods disclosed herein are applicable to industrial and medical purposes.

An industrial application involves a method for preparing an influenza vaccine. Each year, three strains are chosen for selection in that year's flu vaccination by the WHO Global Influenza Surveillance Network. Strains that may be selected include the H1N1, H3N2, and Type-B strains that are believed to be most likely to cause significant human suffering in the coming season. The inventors expect that one of ordinary skill can incorporate the methods disclosed herein in conjunction with conventional vaccine manufacturing processes. An example of a conventional vaccine manufacturing process is disclosed in: Gerdil, C, Vaccine, 2003, 21, 1776-1779 the contents of which are incorporated by reference. Thus, an industrial application is directed to a method of preparing an influenza vaccine, which comprises: identifying at least one influenza virus strain comprising a protein; digesting a composition comprising the protein to obtain a second composition comprising at least one peptide; adding at least one standard peptide to the second composition to obtain a third composition; subjecting the third composition to a liquid chromatograph mass spectrometry (LCMS) assay to obtain a mass of at least one peptide and a mass of at least one standard peptide; and determining a mass ratio of at least one peptide to the mass of at least one standard peptide; and comparing the mass ratio to a calibration curve.

Example 11

Laboratory Procedure Manual for Neuraminidase detection Inactivated whole and split viruses by LC-MS/MS. The method presented here is based on separation of specimen chemical species by liquid chromatography followed by quantification by isotopic dilution and tandem mass spectrometry. Isotope dilution is performed with $C^{13}$- and $N^{15}$-labeled analogs of target peptides. The isotope dilution MS concept involves selecting a specific target peptide as a stoichiometric representative of the protein from which it is cleaved. A known amount of synthetic reference peptide, in which one amino acid has been isotopically labeled, is spiked into the sample. Quantification is achieved by comparing the peak area of the reference peptide with that of an endogenous target peptide that is generated by proteolytic cleavage of the target protein. The benefit of using an isotopically labeled peptide is that any effect of components or additives already in the sample or used during sample preparation will be reflected equally on the native peptide and the labeled peptide. Therefore, the labeled peptide serves to correct for any possible loses during the sample preparation and analysis. To increase selectivity and sensitivity, a multiple reaction monitoring (MRM) assay is applied. This method uses two stages of mass selection (MS/MS): the first stage selects the mass of the intact target peptide, and a second stage monitors one or more specific fragments of the target peptide after it has been exposed to collisions with gas atoms. The two mass filters produce a very specific and sensitive response for the selected analyte. This MS-based approach can provide high structural specificity for the analyte, and in combination with the isotope-dilution (ID) MS, it can provide absolute quantification of analyte concentration.

Reagent samples should be frozen as soon as possible, and stored on dry ice for shipping. The reagent samples should be stored at −70±5° C. until needed. The vaccine samples are stored at 4±2° C. until analysis. After reagent samples are thawed, reconstituted, and mixed with a vortex mixer, the residual samples are stored at room temperature until needed. Vaccine samples are returned to the refrigerator and stored at 4±2° C.

Peptide standards to be stored for extended periods of time should be stored at −20±5° C. when not in use. Standards frequently used to generate calibration curves should be stored at 4±2° C. on the LC autosampler.

Native and Labeled Calibration Standards

Custom synthetic peptides were provided by Sigma Genosys (The Woodlands, Tex.) and are described in Table 2. For YNGIITETIK, a peptide of neuraminidase of H1N1 and H5N1 subtypes, a labeled analog of the target peptide was made by incorporating isoleucine with $^{13}C$ and $^{15}N$ to give a peptide that is 7 Da heavier than the native peptide. An isoleucine of LNVETDTAEIR (of B strains) was also labeled.

For neuraminidase of H5N1 strains, there is a aspartic acid rather than a glutamic acid in the target peptide. Therefore, both peptides were synthesized and labeled to cover all N1 strains. For SGYSGIFSVEGK and LSAGGDIWVTR from N2, a valine was $^{13}$C and $^{15}$N labeled, resulting in peptides, in each case, that are 6 Da heavier than the native peptide. The carboxy terminal lysine of VIEGWSNPNSK of N2 was labeled with $^{13}$C and $^{15}$N resulting in a labeled peptide that was 8 Da heavier than the native. The labeled amino acid is underlined and in bold font in Table 8. These peptides were packaged in 1 nmol/vial quantities by the manufacturer. In addition to the manufacturer's initial amino acid analysis (AAA) necessary for proper vial aliquoting, AAA of the peptide content was independently analyzed at the W.M. Keck Foundation Biotechnology Resource Laboratory at Yale University (New Haven, Conn.) and by Commonwealth Biotechnologies (Richmond, Va.) and will be done using our in-house AAA method.

TABLE 8

Neuraminidase peptides.

| Target Peptide | Influenza Subtype |
|---|---|
| YNGIITETIK (SEQ ID NO 67) | N1 (native) |
| YNGIITETIK (SEQ ID NO 68) | N1 (labeled) |
| YNGIITDTIK (SEQ ID NO 69) | N1 (native) |
| YNGIITDTIK (SEQ ID NO 70) | N1 (labeled) |
| SGYSGIFSVEGK (SEQ ID NO 71) | N2 (native) |
| SGYSGIFSVEGK (SEQ ID NO 72) | N2 (labeled) |
| LSAGGDIWVTR (SEQ ID NO 73) | N2 (native) |
| LSAGGDIWVTR (SEQ ID NO 74) | N2 (labeled) |
| VIEGWSNPNSK (SEQ ID NO 75) | N2 (native) |
| VIEGWSNPNSK (SEQ ID NO 76) | N2 (labeled) |
| LNVETDTAEIR (SEQ ID NO 77) | NB (native) |
| LNVETDTAEIR (SEQ ID NO 78) | NB (labeled) |

The LC-MS/MS method is performed on a Thermo TSQ-Quantum triple quadrupole mass spectrometer (Thermo Scientific, San Jose, Calif.), which is interfaced to a Waters NanoAcquity UPLC system (Waters Corp, Milford, Mass.). Injection is automated using the sample manager of the NanoAcquity system. The mass spectrometer selected reaction monitoring (SRM) configuration is described in Table 9 below. The scan rate is 0.1 sec/scan.

TABLE 9

SRM parameters.

| Target peptide | Observed m/z | ms/ms ion (quantification) | ms/ms ion (confirmation) | ms/ms ion (confirmation) | Collision energy (eV) |
|---|---|---|---|---|---|
| YNGIITETIK (SEQ ID NO 67) | 576.3 (+2) | 704.4 (y6) | 591.3 (y5) | 988.6 (y9) | 23 |
| YNGIITETIK (SEQ ID NO 68) | 639.8 (+2) | 711.4 (y6) | — | — | 23 |
| YNGIITDTIK (SEQ ID NO 69) | 569.3 (+2) | 690.4 (y6) | 577.3 (y5) | 974.6 (y9) | 23 |
| YNGIITDTIK (SEQ ID NO 70) | 572.8 (+2) | 697.4 (y6) | — | — | 23 |
| SGYSGIFSVEGK (SEQ ID NO 71) | 615.8 (+2) | 923.5 (y9) | 836.5 (y8) | 666.3 (y6) | 24 |
| SGYSGIFSVEGK (SEQ ID NO 72) | 618.8 (+2) | 929.5 (Y9) | — | — | 24 |
| LSAGGDIWVTR (SEQ ID NO 73) | 587.8 (+2) | 903.5 (y8) | 974.5 (y9) | 1061.5 (y10) | 23 |
| LSAGGDIWVTR (SEQ ID NO 74) | 590.8 (+2) | 909.5 (y8) | — | — | 23 |
| VIEGWSNPNSK (SEQ ID NO 75) | 615.8 (+2) | 646.3 (y6) | 889.4 (y8) | 1018.5 (y9) | 23 |
| VIEGWSNPNSK (SEQ ID NO 76) | 619.8 (+2) | 654.3 (y6) | — | — | 23 |
| LNVETDTAEIR (SEQ ID NO 77) | 630.8 (+2) | 704.4 (y6) | 805.4 (y7) | 934.4 (y8) | 24 |
| LNVETDTAEIR (SEQ ID NO 78) | 634.3 (+2) | 711.4 (y6) | — | — | 24 |

Calibration samples of all labeled and unlabeled peptides were reconstituted as per the manufacturer's instructions. Twenty µL of 10% (v/v) aqueous formic acid solution was added to the vial containing 1 nmol of peptide. The vial was mixed on a vortex mixer to fully dissolve the peptide. An additional 180 µL of 0.1% formic acid was added to make a 5-pmol/µL stock solution. Working stock solutions of 0.5 pmol/µL of each peptide were prepared from the 5.0-pmol/µL stock solutions via dilution with 0.1% formic acid. Five 0.5-mL stock calibration standards ranging from 10 to 90 fmol/µL were prepared by adding 10, 30, 50, 70, and 90 µL of each of the unlabeled peptides, 50 µL of each of the labeled peptides, and 0.1% formic acid, to make the final volume, 0.5 mL.

A commercial, trivalent, seasonal vaccine was used in this study. Remove the vaccine vial from the refrigerator and allow it to warm to room temperature. Sixty µL of vaccine from 550 (±10) µL vials were diluted in 10 µL of 0.4% Rapigest. The samples were heated for 5 min at 100° C. After cooling to room temperature, 10 µL (~172 µmol) of sequencing grade modified trypsin were added to each sample and incubated at 37° C. for 2 hr. Digests were allowed to cool, and 10 µL of 0.475 M HCl was added to reduce the pH to 2.0 to cleave the acid labile surfactant so that it doesn't interfere with the liquid chromatography method. Using the current sample preparation protocol, only one neuraminidase subtype (using one peptide) can be quantified at a time. 10 µL of the 0.5-pmol/µL solution of either N2, N1, or B labeled ISTD working stock solutions is added. The digested samples were mixed, centrifuged for 10 sec (3,000×g), and transferred to autosampler vials for analysis.

A commercial H5 vaccine was used in this study. Remove the vaccine vial from the refrigerator and allow it to warm to room temperature. Sixty µL of the diluted vaccine is added to 10 µL of 0.4% Rapigest. The samples were heated for 5 min at 100° C. After cooling to room temperature, 10 µL (~172 µmol) of sequencing grade modified trypsin were added to each sample and incubated at 37° C. for 2 hr. Digests were allowed to cool, and 10 uL of 0.475 M HCl was added to reduce the pH to 2.0 to cleave the acid labile surfactant so that it doesn't interfere with the liquid chromatography method].

10 µL of the 0.5-pmol/µL N1 labeled ISTD working stock solution was added for a total sample volume of 100 µL. The digested samples were mixed, centrifuged for 10 sec (3,000× g), and transferred to autosampler vials for analysis.

TABLE 11

Reportable range of results for hemagglutinin

| Compound | Lower reportable limit | Upper reportable limit | Method LOD |
| --- | --- | --- | --- |
| neuraminidase | 10 fmol/µL | 90 fmol/µL | 10 fmol/µL |

Multiple measurements indicate that detection and quantification of 0.4 µg NA per vaccine dose (500 µL) is easily attained. The sensitivity of the method covers the range expected in vaccine preparations. The limit of quantitation (LOQ) of the instrument is 2 fmole injected which corresponds to 126 pg of NA which yields a signal-to-noise ratio of at least 1000:1 on all peptides measured. Thus, simple modifications to the concentrations of Rapigest, internal standards, and trypsin along with the percentage of the digest injected onto the column can result in lower LOQ than the 0.4 µg NA per vaccine dose reported here.

The accuracy of this method relies on 1) complete tryptic digestion of the NA and 2) an accurate concentration of isotopically labeled peptide standard. The tryptic digestion occurs before the addition of the isotopically labeled peptide standard, so it is important to verify that it is complete. To ensure complete digestion of the NA, 1) extensive testing was conducted to assure method parameters were optimized to maximize digestion of NA, 2) trypsin digestion was verified plus additional digestion using other proteolytic enzymes did not increase recovery of target peptides 3) trypsin digestion was verified plus using chemical digestion did not increase recovery of target peptides, and 4) LC/MS/MS demonstrated that incomplete cleavage products that would indicate less than complete digestion were not present. Vaccine samples were first thermally denatured by boiling for 5 minutes and then treated with trypsin for 2 hr with the aid of an acid-labile ionic detergent, Rapigest. Additional parameters which affect protein digestion, including amount of Rapigest, amount of trypsin, time of digestion, and incubation temperature, were optimized to assure maximum digestion of HA. Finally, the digested mixtures were also analyzed by LC/MS/MS for incomplete cleavage products that could affect the quantification. No such incomplete digestion products were found when the vaccines were digested under the final optimized method conditions. The mean protein concentration for each of the three NAs (N1, N2, and B) incubated with trypsin for 1 hr and 24 hr fell within one standard deviation of the values obtained for the 2-hr digests. The proteins of a split virus are completely digested after 1 hr and that the sample preparation time could be shortened if desired. However, separate analysis of whole virus preparations indicates that a minimum of 2-hr incubation with trypsin in the presence of Rapigest is required for complete digestion.

To ensure that the virus was completely digested by the trypsin and to verify the quantification method, two additional peptides that are highly conserved in H5 strains were quantified. FIG. 9 shows that the three peptides chosen are conserved in A/Vietnam/1203/2004, A/Vietnam/1194/2004, and A/Indonesia/05/2005.

These peptides are also conserved in A/Bar-headed goose/QL/1A/2005 and many other strains of clinical interest(data not shown). Using TLDFHDSNVK and LVLATGLR aspeptides for quantification in the same five digest preparations, 37.7±1.30 (3.4%) and 43.1±1.04 (2.4%) fmol/μL were determined for the A/Vietnam/1203/2004 strain. The average of these three numbers, 40.1 fmol/μL, is the amount determined for this viral preparation by use of this isotope dilution LC/MS/MS method.

The second accuracy determinant is the correct concentration of the isotopically labeled peptide standard. After the tryptic digestion, the isotopically labeled peptides are added. In this way, any loss of target peptides in the subsequent method steps would be accounted for, since final quantitation is based on the ratio of target peptide to isotopically labeled peptide.

A medical application involves a method of vaccinating a patient in need thereof. Each year, prior to the onset of flu season, patients routinely visit their healthcare professional in order to receive protection afforded by way of an influenza vaccine. It is contemplated, therefore, a method of vaccinating a patient in need thereof, which comprises: administering to the patient in need thereof a vaccine obtained by a method comprising identifying at least one influenza virus strain comprising a protein; digesting a composition comprising the protein to obtain a second composition comprising at least one peptide; adding at least one standard peptide to the second composition to obtain a third composition; subjecting the third composition to a liquid chromatograph mass spectrometry (LCMS) assay to obtain a mass of at least one peptide and a mass of at least one standard peptide; and determining a mass ratio of at least one peptide to the mass of at least one standard peptide; and comparing the mass ratio to a calibration curve.

References cited or otherwise present herein are indicative of the level of skill in the art to which the invention pertains. These references are hereby incorporated by reference to the same extent as if each individual reference is explicitly and individually incorporated herein. However, in the event that term used herein conflicts with an incorporated term, preference should be given to the term used herein.

REFERENCE LIST

1. Wood, J. M., Developing vaccines against pandemic influenza. *Philos Trans R Soc Lond B Biol Sci* 2001, 356, (1416), 1953-60.
2. Wood, J. M.; Williams, M. S., *History of Inactivated Influenza Vaccines*. Blackwell Science: Oxford, 1998; p 333-345.
3. Schild, G. C.; Wood, J. M.; Newman, R. W., A single-radial-immunodiffusion technique for the assay of influenza haemagglutinin antigen. Proposals for an assay method for the haemagglutinin content of influenza vaccines. *Bull World Health Organ* 1975, 52, (2), 223-31.
4. Wood, J. M.; Schild, G. C.; Newman, R. W.; Seagroatt, V., Application of an improved single-radial-immunodiffusion technique for the assay of haemagglutinin antigen content of whole virus and subunit influenza vaccines. *Dev Biol Stand* 1977, 39, 193-200.
5. Kapteyn, J. C.; Saidi, M. D.; Dijkstra, R.; Kars, C.; Tjon, J. C.; Weverling, G. J.; de Vocht, M. L.; Kompier, R.; van Montfort, B. A.; Guichoux, J. Y.; Goudsmit, J.; Lagerwerf, F. M., Haemagglutinin quantification and identification of influenza A&B strains propagated in PER.C6 cells: a novel RP-HPLC method. *Vaccine* 2006, 24, (16), 3137-44.
6. Garcia-Canas, V.; Lorbetskie, B.; Bertrand, D.; Cyr, T. D.; Girard, M., Selective and Quantitative Detection of Influenza Virus Proteins in Commercial Vaccines Using Two-Dimensional High-Performance Liquid Chromatography and Fluorescence Detection. *Anal Chem* 2007.
7. Rychlik, M.; Mayr, A., Quantitation of N2-[1-(1-carboxy)ethyl]folic acid, a nonenzymatic glycation product of folic acid, in fortified foods and model cookies by a Stable isotope dilution assay. *J Agric Food Chem* 2005, 53, (13), 5116-24.
8. Hachey, D. L.; Coburn, S. P.; Brown, L. T.; Erbelding, W. F.; DeMark, B.; Klein, P. D., Quantitation of vitamin B6 in biological samples by isotope dilution mass spectrometry. *Anal Biochem* 1985, 151, (1), 159-68.
9. Ciner, F. L.; McCord, C. E.; Plunkett, R. W., Jr.; Martin, M. F.; Croley, T. R., Isotope dilution LC/MS/MS for the detection of nerve agent exposure in urine. *J Chromatogr B Analyt Technol Biomed Life Sci* 2007, 846, (1-2), 42-50.
10. Barr, J. R.; Driskell, W. J.; Aston, L. S.; Martinez, R. A., Quantitation of metabolites of the nerve agents sarin, soman, cyclohexylsarin, VX, and Russian VX in human urine using isotope-dilution gas chromatography-tandem mass spectrometry. *J Anal Toxicol* 2004, 28, (5), 372-8.
11. Singh, G.; Arora, V.; Fenn, P. T.; Mets, B.; Blair, I. A., A validated stable isotope dilution liquid chromatography tandem mass spectrometry assay for the trace analysis of cocaine and its major metabolites in plasma. *Anal Chem* 1999, 71, (10), 2021-7.
12. Oe, T.; Ackermann, B. L.; Inoue, K.; Berna, M. J.; Garner, C. O.; Gelfanova, V.; Dean, R. A.; Siemers, E. R.; Holtzman, D. M.; Farlow, M. R.; Blair, I. A., Quantitative analysis of amyloid beta peptides in cerebrospinal fluid of Alzheimer's disease patients by immunoaffinity purification and stable isotope dilution liquid chromatography/negative electrospray ionization tandem mass spectrometry. *Rapid Commun Mass Spectrom* 2006, 20, (24), 3723-35.
13. Cabaleiro, D. R.; Stockl, D.; Kaufman, J. M.; Fiers, T.; Thienpont, L. M., Feasibility of standardization of serum C-peptide immunoassays with isotope-dilution liquid chromatography-tandem mass spectrometry. *Clin Chem* 2006, 52, (6), 1193-6.
14. Mayya, V.; D, K. H., Proteomic applications of protein quantification by isotope-dilution mass spectrometry. *Expert Rev Proteomics* 2006, 3, (6), 597-610.
15. Bronstrup, M., Absolute quantification strategies in proteomics based on mass spectrometry. *Expert Rev Proteomics* 2004, 1, (4), 503-12.
16. Barr, J. R.; Maggio, V. L.; Patterson, D. G., Jr.; Cooper, G. R.; Henderson, L. O.; Turner, W. E.; Smith, S. J.; Hannon, W. H.; Needham, L. L.; Sampson, E. J., Isotope dilution—mass spectrometric quantification of specific proteins: model application with apolipoprotein A-I. *Clin Chem* 1996, 42, (10), 1676-82.
17. Ong, S. E.; Mann, M., Mass spectrometry-based proteomics turns quantitative. *Nat Chem Biol* 2005, 1, (5), 252-62.
18. Fang, T.; Wang, Y.; Ma, Y.; Su, W.; Bai, Y.; Zhao, P., A rapid LC/MS/MS quantitation assay for naringin and its two metabolites in rats plasma. *J Pharm Biomed Anal* 2006, 40, (2), 454-9.
19. Suryawanshi, S.; Singh, S. K.; Gupta, R. C., A sensitive and selective HPLC/ESI-MS/MS assay for the simultaneous quantification of 16-dehydropregnenolone and its major metabolites in rabbit plasma. *J Chromatogr B Analyt Technol Biomed Life Sci* 2006, 830, (1), 54-63.
20. Wang, J.; Cheung, W., Determination of pesticides in soy-based infant formula using liquid chromatography with electrospray ionization tandem mass spectrometry. *J AOAC Int* 2006, 89, (1), 214-24.
21. Sambrook, J.; Fritsch, E. F.; Maniatis, T., *Molecular Cloning: A Laboratory Manual*. 2 ed.; Cold Spring Harbor Laboratory Press: 1989.
22. Clauser, K. R.; Baker, P.; Burlingame, A. L., Role of accurate mass measurement (+/−10 ppm) in protein identification strategies employing MS or MS/MS and database searching. *Anal Chem* 1999, 71, (14), 2871-82.
23. Mo, W.; Ma, Y.; Takao, T.; Neubert, T. A., Sequencing of oxidized methionine-containing peptides for protein identification. *Rapid Commun Mass Spectrom* 2000, 14, (21), 2080-1.
24. Taylor, S. W.; Fahy, E.; Murray, J.; Capaldi, R. A.; Ghosh, S. S., Oxidative post-translational modification of tryptophan residues in cardiac mitochondrial proteins. *J Biol Chem* 2003, 278, (22), 19587-90.
25. Biotechnology, N. C. f. Influenza Virus Resource. http://www.ncbi.nlm.nih.gov/genomes/FLU/ (Feb. 17, 2007).
26. Edgar, R., MUSCLE: multiple sequence alignment with high accuracy and high throughput. *Nucleic Acids Res* 2004, 32, (5), 1792-1797.
27. Holm, S. S.; Hansen, S. H.; Faber, J.; Staun-Olsen, P. *Clin. Biochem.* 2004, 37, 85-93.
28. DiMarco, T.; Giulivi, C. *Mass Spectrom Rev* 2007, 26, 108-120.
29. Hernández, F.; Sancho, J. V.; Pozo, O. J. *Anal. Bioanal. Chem.* 2005, 382, 934-946.
30. Johnson, R. C.; Lemire, S. W.; Woolfitt, A. R.; Ospina, M.; Preston, K. P.; Olson, C. T.; Barr, J. R. *J. Anal. Toxicol.* 2005, 29, 149-155.
31. Blair, I. A.; Tilve, A. *Curr. Drug Metab.* 2002, 3, 463-480.

32. Dooley, K. C. *Clin Biochem* 2003, 36, 471-481.
33. Kirkpatrick, D. S.; Gerber, S. A.; Gygi, S. P. *Methods* 2005, 35, 265-273.
34. Mayya, V.; Rezual, K.; Wu, L.; Fong, M. B.; Han, D. K. *Mol. Cell. Proteomics* 2006, 5, 1146-1157.
35. Brönstrup, M. *Expert Rev. Proteomics* 2004, 1, 503-512.
36. Gerber, S. A.; Rush, J.; Stemman, O.; Kirschner, M. W.; Gygi, S. P. *Proc. Natl. Acad. Sci.* 2003, 100, 6940-6945.
37. Barr, J. R.; Maggio, V. L.; Patterson, D. G., Jr.; Cooper, G. R.; Henderson, L. O.; Turner, W. E.; Smith, S. J.; Hannon, W. H.; Needham, L. L.; Sampson, E. J. *Clin. Chem.* 1996, 42, 1676-1682.
38. Williams, T. L.; Luna, L. G.; Guo, Z.; Donis, R. O.; Cox, N.; Pirkle, J. L.; Barr, J. R. 2007, submitted.
39. Wu, N.; Clausen, A., M *J Sep Sci* 2007, 30, 1167-1182.
40. Churchwell, M. I.; Twaddle, N. C.; Meeker, L. R.; Doerge, D. R. *J. Chromatogr. B* 2005, 825, 134-143.
41. Nováková, L.; Matysová, L.; Solich, P. *Talanta* 2006, 68, 908-918.
42. Li, R.; Dong, L.; Huang, *J. Anal. Chim Acta* 2005, 546, 167-173.
43. Loboda, A. V.; Krutchinsky, A. N.; Bromirski, M.; Ens, W.; Standing, K. G. *Rapid Comm Mass Spectrom* 2000, 14, 1047-1057.
44. Barcelo-Barrachina, E.; Moyano, E.; Galceran, M. T.; Lliberia, J. L.; Bago, B.; Cortes, M. A. *J. Chromatogr. A* 2006, 1125, 195-203.
45. New, L.-S.; Saha, S.; Ong, M. K.; Boelsterli, U. A.; Chan, E. *Rapid Comm Mass Spectrom* 2007, 21, 982-988.
46. Mezcua, M.; Aguera, A.; Lliberia, J. L.; Cortes, M. A.; Bago, B.; Fernandez-Alba, A. R. *J. Chromatogr. A* 2006, 1109, 222-227.
47. Wang, X.; Zhao, T.; Gao, X.; Dan, M.; Zhou, M.; Jia, W. *Anal. Chim. Acta* 2007, 594, 265-273.
48. Zhang, Y.; Jiao, J.; Cai, Z.; Zhang, Y.; Ren, Y. *J. Chromatogr. A* 2007, 1142, 194-198.
49. Al-Dirbashi, O.; Aboul-Enein, H.; Jacob, M.; Al-Qahtani, K.; Rashed, M. *Anal. Bioanal. Chem.* 2006, 385, 1439-1443.
50. Leandro, C. C.; Hancock, P.; Fussell, R. J.; Keely, B. J. *J. Chromatogr. A* 2007, 1144, 161-169.
51. Ma, Y.; Qin, F.; Sun, X.; Lu, X.; Li, F. *J. Pharm. Biomed. Anal.* 2007, 43, 1540-1545.
52. Mensch, J.; Noppe, M.; Adriaensen, J.; Melis, A.; Mackie, C.; Augustijns, P.; Brewster, M. E. *J. Chromatogr. B* 2007, 847, 182-187.
53. Salquèbre, G.; Bresson, M.; Villain, M.; Cirimele, V.; Kintz, P. *J. Anal. Toxicol.* 2007, 31, 114-118.
54. Yu, K.; Di, L.; Kerns, E.; Li, S. Q.; Alden, P.; Plumb, R. S. *Rapid Comm Mass Spectrom* 2007, 21, 893-902.
55. Clauser, K. R.; Baker, P.; Burlingame, A. L. *Anal Chem* 1999, 71, 2871-2882.

The invention claimed is:

1. A process of quantifying a protein, which comprises:
digesting a composition comprising the protein to obtain a second composition comprising at least one peptide;
adding at least one standard peptide to the second composition to obtain a third composition;
subjecting the third composition to a liquid chromatography mass spectrometry (LCMS) assay to obtain a mass of at least one peptide and a mass of at least one standard peptide; and
determining a mass ratio of at least one peptide to the mass of at least one standard peptide; and
comparing the mass ratio to a calibration curve, wherein said calibration curve is a mathematical relationship between a known amount of said peptide and the quotient of the known amount of said peptide and a constant amount of said standard peptide.

2. The process of claim 1, wherein the protein is a viral protein, a bacterial protein, a protozoan protein, a fungal protein, a prion, a glycoprotein, a lipoprotein, a glyco-lipoprotein, or a eukaryotic protein.

3. The process of claim 2, wherein the viral protein is a protein obtained from an influenza virus.

4. The process of claim 3, wherein the influenza virus comprises at least one of the hemagglutinin subtypes of H1, H3, H5, or HB.

5. The process of claim 1, wherein the protein is obtained from an influenza virus and is selected from among a hemagglutinin, a neuraminidase, a nucleoprotein, or a matrix protein.

6. The process of claim 1, wherein the second composition further comprises an endoprotease.

7. The process of claim 6, wherein the endoprotease is trypsin.

8. The process of claim 6, wherein the composition further comprises a surfactant.

9. The process of claim 1, wherein the amino acid sequence of the at least one peptide and the at least one standard peptide are the same.

10. The process of claim 1, wherein the mass of the at least one peptide and the mass of the at least one standard peptide are not the same.

11. The process of claim 10, wherein the at least one standard peptide comprises at least one isotopically-enriched amino acid.

12. The process of claim 11, wherein the at least one isotopically-enriched amino acid comprises at least one isotope selected from among $^{13}C$ and $^{15}N$.

13. The process of claim 1, wherein the at least one peptide comprises one or more of SEQ ID NOs: 1, 3, 5, or 7.

14. The process of claim 1, wherein the protein is obtained from one or more of the following *Escherichia coli, Mycobacterium tuberculosis, Bacillus anthracis, Salmonella, Staphylococcus aureus, Streptococcus pneumoniae, Haemophilus influenzae, Streptococcus pyogenes, Helicobacter pylori, Francisella tularensis, Klebsiella pneumoniae, Bacillus anthracis, Burkholderia mallei, Burkholderia pseudomallei*, hepatitis A, hepatitis B, hepatitis C, hepatitis D, hepatitis E, herpes simplex virus, molluscum contagiosum virus, human immunodeficiency virus, *Cryptosporidium, Giardia lamblia, Plasmodium, Trypanosoma cruzi, Pneumocystis jirovecii, Tinea, Candida, Histoplasma capsulatum, Cryptococcus neoformans*, roundworm, and tapeworm.

15. The process of claim 1, wherein the LCMS assay is a liquid chromatograph isotope dilution mass spectrometry assay.

16. The process of claim 1, wherein said LCMS assay comprises fragmenting the at least one peptide and the at least one standard peptide and measuring the masses of the fragments of the at least one peptide and the masses of the fragments of the at least one standard peptide.

17. A process of quantifying a protein, which comprises:
subjecting a composition comprising at least one peptide and at least one standard peptide to a liquid chromatography mass spectrometry (LCMS) assay to obtain a mass of at least one peptide and a mass of at least one standard peptide; and determining a mass ratio obtained by dividing the mass of at least one peptide and the mass of at least one standard peptide; and comparing the mass ratio to a calibration curve, wherein said calibration curve is a mathematical relationship between a known amount of said peptide and the quotient of the known amount of said peptide and a constant amount of said standard peptide.

18. The process of claim 17, wherein said subjecting comprises fragmenting the at least one peptide and the at least one standard peptide and measuring the masses of the fragments the at least one peptide to the masses of the fragments of the at least one standard peptide.

19. A method of preparing an influenza vaccine, which comprises:

identifying at least one influenza virus strain comprising a protein;

digesting a composition comprising the protein to obtain a second composition comprising at least one peptide;

adding at least one standard peptide to the second composition to obtain a third composition;

subjecting the third composition to a liquid chromatograph mass spectrometry (LCMS) assay to obtain a mass of at least one peptide and a mass of at least one standard peptide; and determining a mass ratio of at least one peptide to the mass of at least one standard peptide; and comparing the mass ratio to a calibration curve, wherein said calibration curve is a mathematical relationship between a known amount of said peptide and the quotient of the known amount of said peptide and a constant amount of said standard peptide.

* * * * *